United States Patent
Chaudhuri et al.

(10) Patent No.: US 7,150,876 B2
(45) Date of Patent: Dec. 19, 2006

(54) METHODS FOR STABILIZING INGREDIENTS WITHIN COSMETICS, PERSONAL CARE AND HOUSEHOLD PRODUCTS

(75) Inventors: Ratan Chaudhuri, Lincoln Park, NJ (US); Germain Puccetti, Yorktown Heights, NY (US); Francois Marchio, Scarsdale, NY (US); Zoia Lascu, Middle Village, NY (US)

(73) Assignee: Merck Patent GmbH, Darmstadt (DE)

( * ) Notice: Subject to any disclaimer, the term of this patent is extended or adjusted under 35 U.S.C. 154(b) by 22 days.

(21) Appl. No.: 11/115,395

(22) Filed: Apr. 27, 2005

(65) Prior Publication Data

US 2005/0244349 A1 Nov. 3, 2005

Related U.S. Application Data

(60) Provisional application No. 60/565,843, filed on Apr. 28, 2004.

(51) Int. Cl.
*A61K 2/00* (2006.01)

(52) U.S. Cl. .................................................... 424/401
(58) Field of Classification Search ............... 424/400, 424/401
See application file for complete search history.

(56) References Cited

U.S. PATENT DOCUMENTS

| | | |
|---|---|---|
| 6,602,515 B1 | 8/2003 | Chaudhuri |
| 6,699,463 B1 | 3/2004 | Chaudhuri |

*Primary Examiner*—Shelley A. Dodson
(74) *Attorney, Agent, or Firm*—Millen, White, Zelano & Branigan PC

(57) ABSTRACT

The present invention relates to methods and compositions for using photostabilizer compounds for stabilizing formulation ingredients, like flavors, fragrances, colors, antioxidants, polymers, within cosmetics, personal care and household products, against degradation from sun light, heat and air oxidation resulting in improvement in storage stability, viscosity, and maintenance of color of the formulated products.

58 Claims, 3 Drawing Sheets

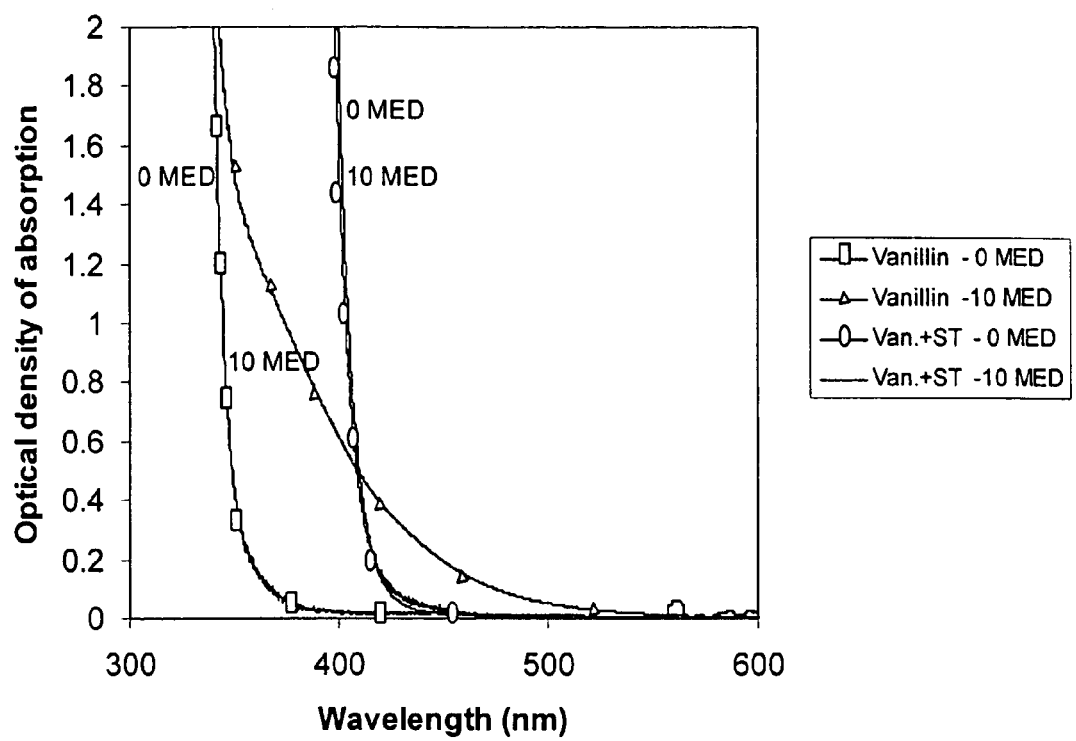
Figure 1: Color change of Vanillin (van.) in solution under sun simulator with and without Diethyhexyl syringylidene malonate (ST) in solution. (Dosage in MED)

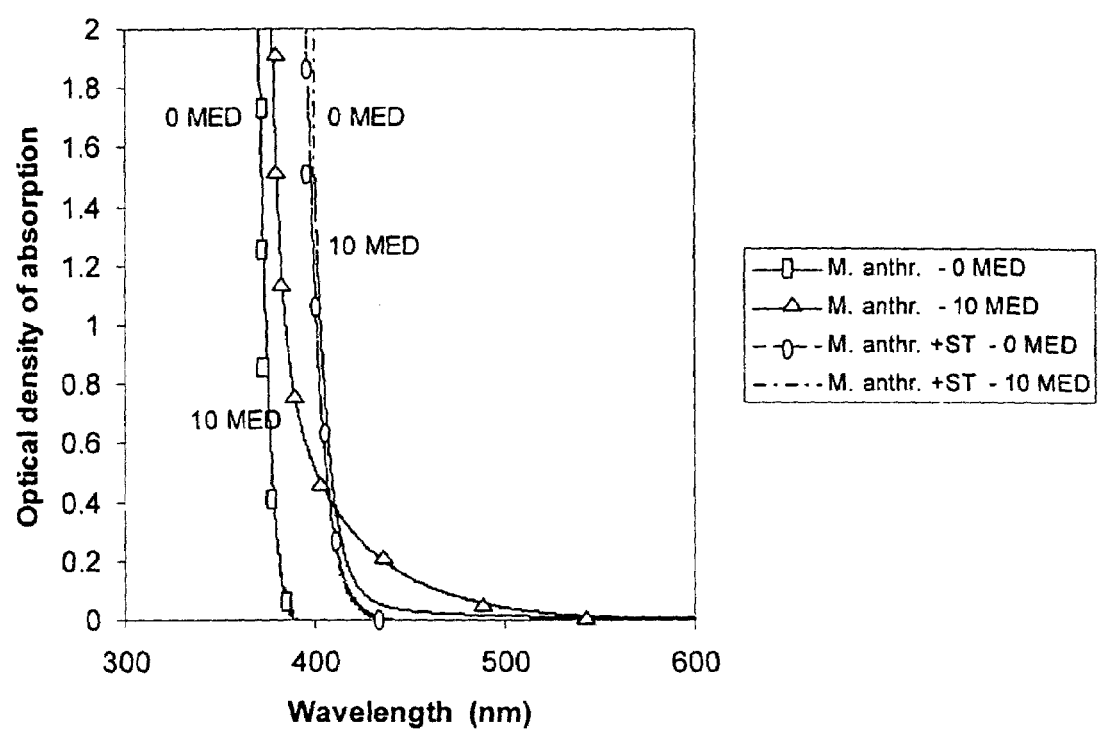
Figure 2: Color change of Menthyl anthranilate (M. anthr.) under sun simulator with and without Diethyhexyl syringylidene malonate (ST) in solution. (Dosage in MED)

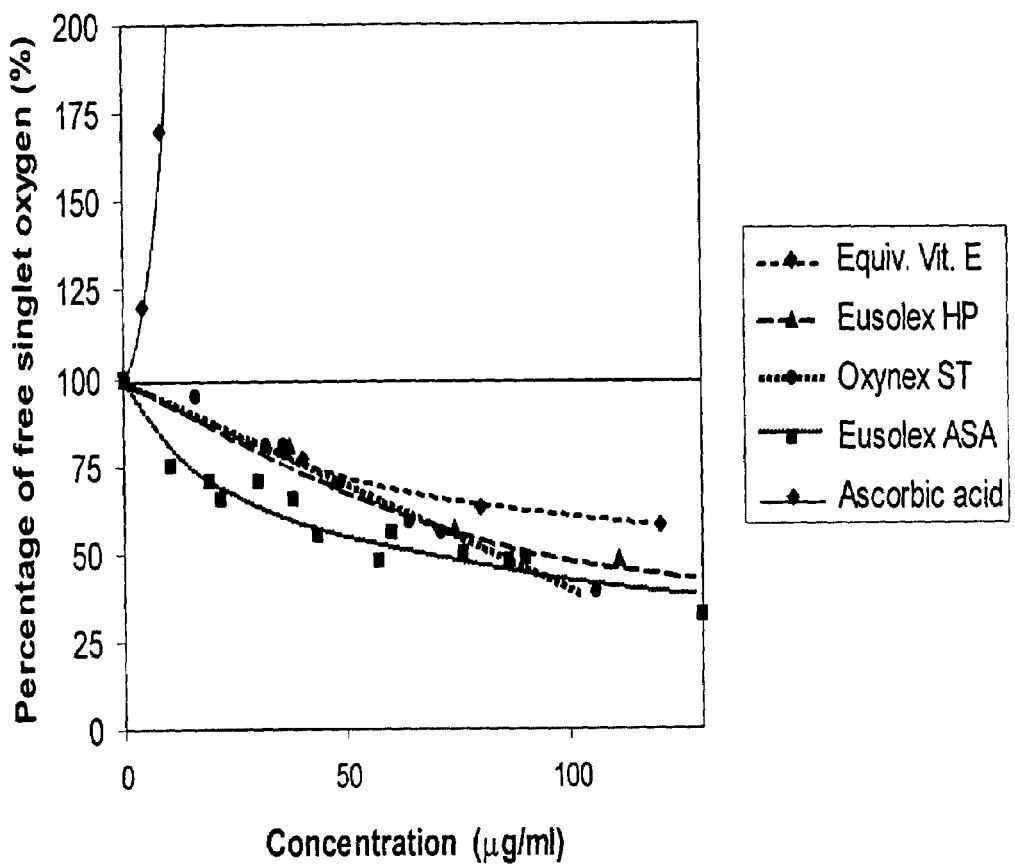
Figure 3: Singlet oxygen scavenging properties of compounds of present invention (Eusolex HP = Bis – N [3' –(N,N dimethylamino) propyl]-3,5-dimethoxy -4 hydroxybenzylidene malonamide bis ethyl sulfate; Oxynex ST = Diethyhexyl syringylidene malonate, Eusolex ASA = Isoamyl alpha acetyl -3,5 dimethoxy 4 hydroxy benzylidene malonate)and Vitamin E and Ascorbic Acid.

ns to methods for using photostabilizer compounds to stabilize formulation ingredients, like, for example, flavors, fragrances, colors, antioxidants, and polymers against degradation from sun light, heat and air oxidation resulting in improvement in storage stability, viscosity, and maintenance of color of the formulated products.

BACKGROUND OF THE INVENTION

U.S. Pat. No. 6,602,515, copending application Ser. No. 10/022,343, filed Dec. 20, 2001, and U.S. Pat. No. 6,699,463 describe compounds of general formulae i, i' and i", respectively.

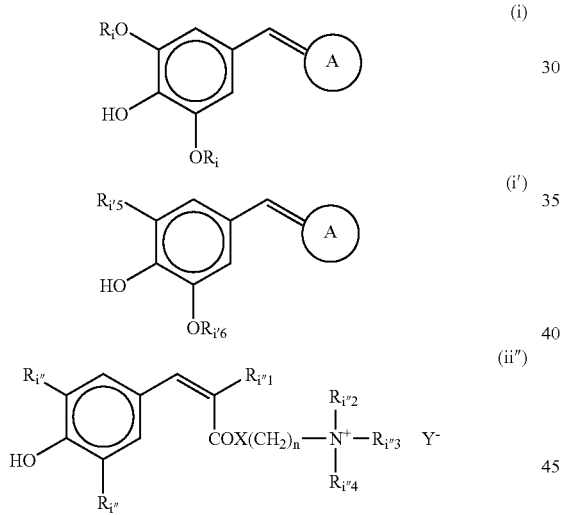

with A and R groups as defined more particularly below. These compounds have sunscreen activity, i.e., they have a chromophoric moiety which absorbs within the ultra violet range from 290–400 nm. These compounds also exhibit antioxidant properties which preserve other UV absorbers within sunscreen formulations. They are typically used in sunscreen formulations in amounts of 2 to 10 wt % based on the total weight of the sunscreen formulation.

Light is a form of energy. Therefore molecules that are able to absorb UV and visible light such as organic colorants, dyes, antioxidants, fragrances, & flavor ingredients, can be elevated to a higher energy level (excited state) upon absorption of radiation. In this state, molecules are more reactive than in the ground state. They may react with other molecules or breakdown into lower energy degradation products resulting in complete loss of product integrity, color loss, malodor, viscosity changes etc. The probability of reaction or decomposition is directly related to the length of time molecules remain in the excited state.

The absorption of UV light by UV absorbing chromophores does not block all potential degradation pathways for photosensitive compounds. Another approach to avoid (UV-) light induced decomposition is the quenching of excited chromophores. Quenching of excited chromophores reduces the lifetime of excited states thereby reducing the side reactions of excited state intermediates. This results in an extended shelf life for formulated products. Combining UV-light absorbing capability with the ability to quench the excited state within a single molecule is desired.

DESCRIPTION OF THE INVENTION

Many poly-unsaturated and aromatic compounds used as ingredients in cosmetics, personal care and household products are not always photochemically stable, which limits their utility. Examples of such compounds include colorants, antioxidants, flavors and fragrances. More specific examples include carotenoids, tocopherols, guaiazulene, vanillin and menthylanthranillate. Many polymers having no unsaturation, used as thickening agents in cosmetics or personal or household products, are also susceptible to degradation under heat, sun light or extended storage in room temperature due to free radical formation under these conditions resulting in the drop in the viscosity.

It has now been discovered that the dialkylbenzalmalonates, monoalkyl-monoacyl benzalmalonate, dialkyl benzalmalonamide and mono-alkyl-monoacyl benzalmalonamide compounds of formulae i, i' and i'"

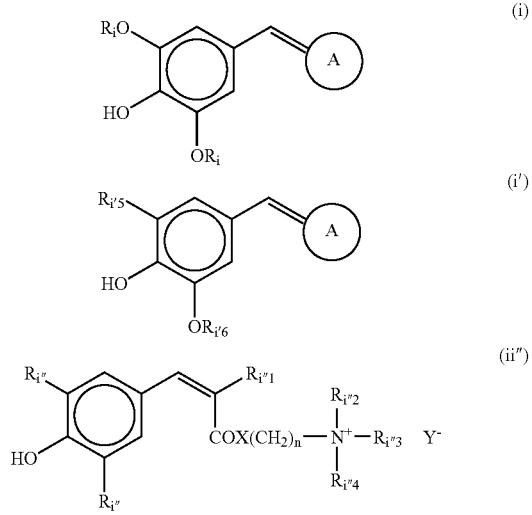

are able to stabilize photo-sensitive ingredients within formulations such as cosmetics, personal care products and household products.

It is well known that a wide range of aromatic compounds, such as, organic dyes, naphthalene and anthracene derivatives, some organic sunscreens (Octylmethoxy Cinnamate, Octyldimethyl PABA), microfine titanium dioxide (Un-coated or inadequately coated) and microfine zinc oxide (Un-coated or inadequately coated) etc, when exposed to UV or visible light generates excited states that can undergo rapid and efficient energy transfer to oxygen to give singlet oxygen. Energy transfer to yield singlet oxygen usually competes with electron transfer, so many phosensitizers give both singlet oxygen and super oxide anion. The yield of singlet oxygen vs. super oxide anion is therefore dependent on the sensitizer, the excitation wavelength, and the reaction conditions. Products used in this invention are also excellent quenchers for both singlet oxygen and super oxide anion thereby providing improved stabilization of formulation ingredients.

This combined "boosting effect" observed with the products of the present invention not only provides product stabilization effects beyond what was previously possible, but also offers synergistic, cost-effective solutions of product stabilization.

In formulae i and i', A is a moiety which provides chromophoric properties within the UV radiation range of 290–400 nm. This moiety comprises one divalent group or two monovalent groups with at least one group having carbonyl (C=O) functionality.

For formula i, each $R_i$ is independently linear or branched $C_1$–$C_8$ alkyl.

For formula i', $R_{i'6}$ is linear or branched $C_1$–$C_8$ alkyl and $R_{i'5}$ is hydrogen or linear or branched $C_1$–$C_8$ alkyl.

For formula i", each $R_{i''}$ is independently linear or branched $C_1$ to $C_8$ alkyl, or linear or branched $C_1$ to $C_8$ alkoxy; or one $R_{i''}$ is H and the other $R_{i''}$ is linear or branched $C_1$ to $C_8$ alkyl, or linear or branched $C_1$ to $C_8$ alkoxy. $R_{i''1}$ is $COCH_3$, $CO_2R_{i''5}$, $CONH_2$, $CON(R_{i''6})_2$, CN, $COX(CH_2)n-N-(R_{i''2})(R_{i''4})(R_{i''3})$, and the quaternized salt form of the formula $COX(CH_2)n-N-(R_{i''2})(R_{i''4})(R_{i''3})^+Y^-$; X is O, NH or N-alkyl, wherein Alkyl is, for example, $C_{1-8}$ Alkyl, preferably $C_{1-4}$ Alkyl, more preferably Methyl or Ethyl, most preferably Methyl; n is an integer of 1 to 5; Y is an anion; $R_{i''2}$, $R_{i''3}$ and $R_{i''4}$ are independently linear or branched $C_1$ to $C_{20}$ alkyl; and $R_{i''5}$ and $R_{i''6}$ are independently hydrogen or linear or branched $C_1$–$C_{20}$ alkyl.

Preferred compounds of formulae i, i' and i" are of formulae ii, ii', and ii", respectively.

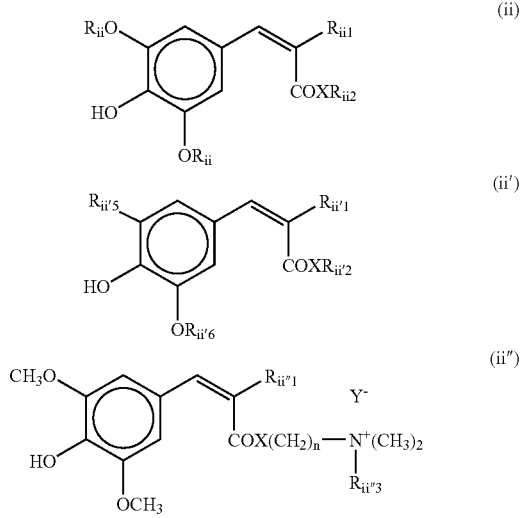

For formula ii,
each $R_{ii}$ is independently linear or branched $C_1$ to $C_8$ alkyl;
$R_{ii1}$ is $-C(O)CH_3$, $-CO_2R_{ii3}$, $-C(O)NH_2$, $-C(O)N(R_{ii4})_2$, or $-CN$;
X is O, NH or N-alkyl, wherein Alkyl is, for example, $C_{1-8}$ Alkyl, preferably $C_{1-4}$ Alkyl, more preferably Methyl or Ethyl, most preferably Methyl;
$R_{ii2}$ is linear or branched $C_1$ to $C_{20}$ alkyl;
$R_{ii3}$ is linear or branched $C_1$ to $C_{20}$ alkyl; and
each $R_{ii4}$ is independently hydrogen or linear or branched $C_1$ to $C_8$ alkyl.

For formula ii',
$R_{ii'1}$ is $-C(O)CH_3$, $-CO_2R_{ii'3}$, $-C(O)NH_2$, $-C(O)N(R_{ii'4})_2$, or $-CN$;
X is O, NH or N-alkyl, wherein Alkyl is, for example, $C_{1-8}$ Alkyl, preferably $C_{1-4}$ Alkyl, more preferably Methyl or Ethyl, most preferably Methyl;
$R_{ii'2}$ is linear or branched $C_1$ to $C_{30}$ alkyl;
$R_{ii'3}$ is linear or branched $C_1$ to $C_{20}$ alkyl;
each $R_{ii'4}$ is independently hydrogen or linear or branched $C_1$ to $C_8$ alkyl;
$R_{ii'5}$ is linear or branched $C_1$–$C_8$ alkyl or hydrogen; and
$R_{ii'6}$ is linear or branched $C_1$–$C_8$ alkyl.

For formula ii",
$R_{ii''1}$ is defined as $R_{i''1}$ for formula i", and is preferably $COCH_3$ or $CONH(CH_2)_3N^+(CH_3)_2(CH_2CH_3)$ $CH_3CH_2OSO^-_3$;
X is O, NH or N-alkyl, wherein Alkyl is, for example, $C_{1-8}$ Alkyl, preferably $C_{1-4}$ Alkyl, more preferably Methyl or Ethyl, most preferably Methyl,
$R_{ii''3}$ is linear or branched $C_1$ to $C_{20}$ alkyl; and
$Y^-$ is an anion.

Included within the preferred compounds are those of formula ii wherein $R_{ii}$ is linear or branched $C_1$–$C_4$ alkyl, X is oxygen and $R_{ii2}$ is linear or branched $C_1$–$C_{12}$ alkyl. Of these compounds, those more preferred have $R_{ii1}$ as $C(O)CH_3$ or $CO_2R_{ii3}$ wherein $R_{ii3}$ is a linear or branched $C_1$ to $C_8$ alkyl. For compounds wherein $R_{ii1}$ is $C(O)N(R_{ii4})_2$, $R_{ii4}$ is preferably hydrogen or a linear or branched $C_1$–$C_4$ alkyl.

Included within the preferred compounds are those of formula ii' wherein $R_{ii'1}$ is linear or branched $C_1$–$C_4$ alkyl, X is oxygen and $R_{ii'2}$ is linear or branched $C_1$–$C_{12}$ alkyl. Of these compounds, those more preferred have $R_{ii'1}$ as $C(O)CH_3$ or $CO_2R_{ii'3}$ wherein $R_{ii'3}$ is a linear or branched $C_1$ to $C_8$ alkyl. For compounds wherein $R_{ii'1}$ is $C(O)N(R_{ii'4})_2$, $R_{ii'4}$ is preferably hydrogen or a linear or branched $C_1$–$C_4$ alkyl.

While compounds having from $C_1$–$C_8$ alkyl groups for $R_{ii2}$, $R_{ii'2}$, $R_{ii3}$, and $R_{ii'3}$ for compounds of formula ii and ii' are preferred, significant utility can be obtained from compounds wherein $R_{ii2}$, $R_{ii'2}$, $R_{ii3}$, and $R_{ii'3}$ are linear or branched $C_9$ to $C_{20}$ alkyl or $C_{12}$ to $C_{20}$ alkyl groups.

Concerning formulae i" and ii", the integer n is preferably 2 to 3; and the anion $Y^-$ is preferably Cl, Br, alkyl sulfate, alkyl sulfonate, or p-tolyl sulfonate. $R_{i''2}$, $R_{i''3}$, $R_{i''4}$ and $R_{ii''3}$ of formulae i" and ii" are preferably independently linear or branched $C_1$ to $C_8$. $R_{i''5}$, $R_{i''6}$, $R_{ii''5}$ and $R_{ii''6}$ are preferably $C_1$ to $C_8$ alkyl.

Another preferred class of compounds are those of formulae iii and iv and iii' and iv'

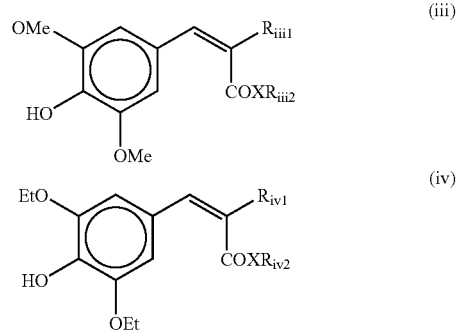

-continued

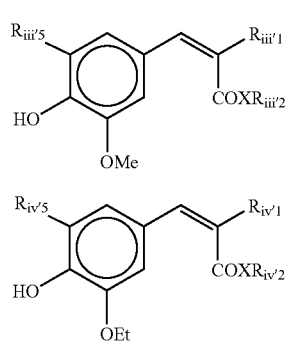

wherein
$R_{iii1}$ is —C(O)CH$_3$, —CO$_2$R$_{ii3}$, —C(O)NH$_2$, —C(O)N(R$_{ii4}$)$_2$, or —CN,
$R_{iii2}$ is linear or branched C$_1$ to C$_{20}$ alkyl,
$R_{iv1}$ is —C(O)CH$_3$, —CO$_2$R$_{ii3}$, —C(O)NH$_2$, —C(O)N(R$_{ii4}$)$_2$, or —CN,
$R_{iv2}$ is linear or branched C$_1$ to C$_{20}$ alkyl,
$R_{iii'1}$ is —C(O)CH$_3$, —CO$_2$R$_{ii'3}$, —C(O)NH$_2$, —C(O)N(R$_{ii'4}$)$_2$, or —CN,
$R_{iii'2}$ is linear or branched C$_1$ to C$_{30}$ alkyl,
$R_{iii'5}$ is linear or branched C$_1$-C$_8$ alkyl or hydrogen,
$R_{iv'1}$ is —C(O)CH$_3$, —CO$_2$R$_{ii'3}$, —C(O)NH$_2$, —C(O)N(R$_{ii'4}$)$_2$, or —CN,
$R_{iv'2}$ is linear or branched C$_1$ to C$_{30}$ alkyl, and
$R_{iv'5}$ is linear or branched C$_1$-C$_8$ alkyl or hydrogen.
R groups within these definitions are as defined above.
Preferred compounds of Formulae i, ii, iii and iv include:
ethyl-alpha-cyano-3,5-dimethoxy-4-hydroxy cinnamate,
ethyl-alpha-acetyl-3,5-dimethoxy-4-hydroxy cinnamate,
iso-propyl-alpha-acetyl-3,5-dimethoxy-4-hydroxy cinnamate,
iso-amyl-alpha-acetyl-3,5-dimethoxy-4-hydroxy cinnamate,
2-ethylhexyl-alpha-acetyl-3,5-dimethoxy-4-hydroxy cinnamate,
diethyl-3,5-dimethoxy-4-hydroxy benzylidene malonate,
di-(2-ethylhexyl)-3,5-dimethoxy-4-hydroxy benzylidene malonate,
diisoamyl-3,5-dimethoxy-4-hydroxy benzylidene malonate,
didodecyl-3,5-dimethoxy-4 hydroxy benzylidene malonate,
dipalmitoyl-3,5-dimethoxy-4-hydroxy benzylidene malonate, and
di-isopropyl-3,5-dimethoxy-4-hydroxy benzylidene malonate.
Preferred compounds of Formulae i', ii', iii' and iv' include:
ethyl-alpha-cyano-3-methoxy-4-hydroxy cinnamate,
ethyl-alpha-acetyl-3-methoxy-4-hydroxy cinnamate,
iso-propyl-alpha-acetyl-3-methoxy-4-hydroxy cinnamate,
iso-amyl-alpha-acetyl-3-methoxy-4-hydroxy cinnamate,
2-ethylhexyl-alpha-acetyl-3-methoxy-4-hydroxy cinnamate,
diethyl-3-methoxy-4-hydroxy benzylidene malonate,
di-(2-ethylhexyl)-3-methoxy-4-hydroxy benzylidene malonate,
diisoamyl-3-methoxy-4-hydroxy benzylidene malonate,
didodecyl-3-methoxy-4-hydroxy benzylidene malonate,
dipalmitoyl-3-methoxy-4-hydroxy benzylidene malonate, and
di-isopropyl-3-methoxy-4-hydroxy benzylidene malonate.

Preferred compounds of Formulae i'' and ii'' include:

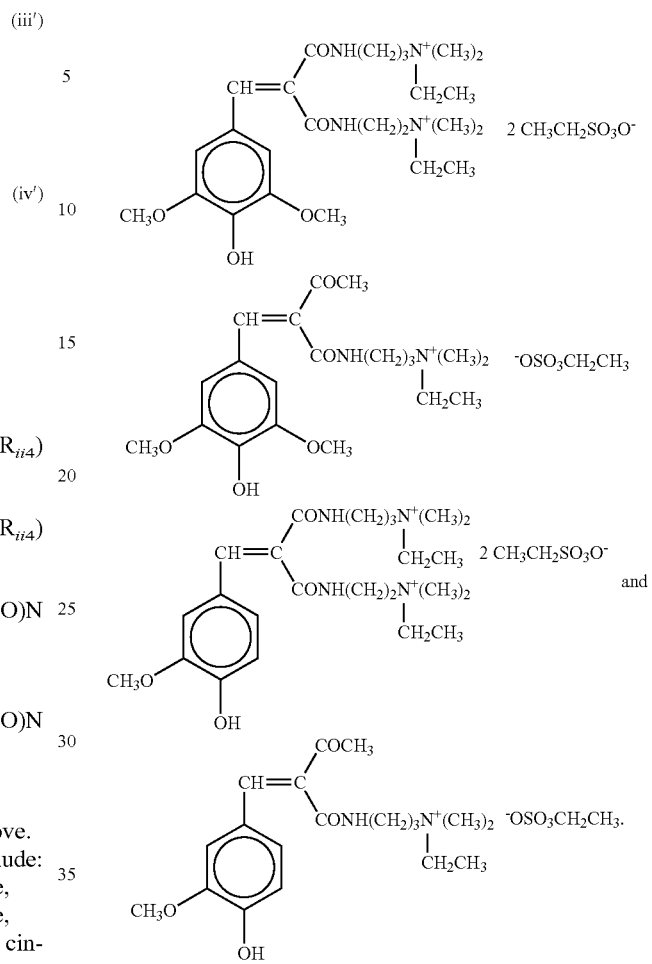

The anion used is not restricted and may be any anion. Illustrative useful anions are, for example, chloride, bromide, tosylate and/or methosulfate.

A method provided by this invention comprises combining at least one compound of formulae i, i', i'', ii, ii', ii'', iii, iii', iv and/or iv' with at least one photosensitive poly-unsaturated or aromatic compound which is either a color compound, a fragrance compound, a flavor compound, antioxidant or a combination of these compounds (color/fragrance/flavor/antioxidant). Additionally, photosensitive polymeric compounds, which may not have any aromatic or poly-unsaturated functionality, are also part of this invention.

In another aspect, a method is provided for stabilizing at least one photosensitive poly-unsaturated and/or aromatic compound which is either a color compound, antioxidant, a fragrance compound, a flavor compound or a combination thereof, includes combining at least one compound of formulae i, i', i'', ii, ii', ii'', iii, iii', iv and/or iv' with said at least one photosensitive poly-unsaturated and/or aromatic compound in a ratio within a range of 20:1 to 1:5, preferably 10:1 to 1:1 or 1:2, more preferably 5:1 to 2:1 or 1:1, based on total weight percent of the one or more compounds of formulae i, i', i'', ii, ii', ii'', iii, iii', iv and/or iv' to the total weight percent of the one or more photosensitive poly-unsaturated and/or aromatic compounds. A polymeric thickening agent may also be stabilized likewise.

Stabilizing compounds that are photosensitive in the context of this invention means reducing the degradation of these photosensitive compounds, which have absorbed visible light or UV rays to form high energy chromophores. Thus, the phrase "photosensitive in the visible light range" refers to compounds that form unstable chromophores once visible light is absorbed which may or may not be stable once UV radiation is absorbed. Accordingly, compounds or compositions that are only exposed to visible light, or substantially or predominantly only to visible light, for example, during storage in a warehouse, on a shelf in a store or in a home, are protected. Protection continues even when protected compounds by the methods of the invention are exposed to natural sunlight that contains both UV and visible light.

In preferred embodiments, combinations according to the invention are formed within or transferred to a cosmetic composition, personal care product or household product. In a further preferred embodiment, the cosmetic composition, personal care product or household product is within a container for retail sale when the combination is formed or transferred to a container for retail sale after the combination is formed.

The weight percent of the compound of formula i, i', i", ii, ii', ii", iii, iii', iv and/or iv' is 0.001–10.0, preferably 0.01–4.0, more preferably 0.01–2.0, even more preferably 0.1–1.0, and most preferably 0.02–0.5 wt % in the cosmetic composition, personal care product or household product.

In other preferred embodiments, however, one or more color compounds, one or more fragrance compounds, or one or more flavor compounds is/are brought together with a compound of formula i, i', i", ii, ii', ii", iii, iii', iv and/or iv' without substantially any other ingredients (other ingredients however may be present). The stabilizer compounds of the invention are effective in compositions that contain only a color compound, a fragrance compound, or a flavor compound is brought together with a compound of formula i, i', i", ii, ii', ii", iii, iii', iv and/or iv'. The ratio of a compound of formula i, i', i", ii, ii', ii", iii, iii', iv and/or iv' to a color compound, a fragrance compound, or a flavor compound in these compositions is as described above. Preferred is a composition where a fragrance is stabilized.

In other aspects, vitamins can likewise be stabilized by a compound of formula i, i', i", ii, ii', ii", iii, iii', iv and/or iv'. All vitamins are included and their derivatives as they are subject to photodegradation. Vitamins and vitamin derivatives are, for example, vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C and derivatives (for example ascorbyl palmitate, magnesium ascorbyl phosphate, ascorbyl acetate), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$). Preferred vitamins are, for example, vitamin A palmitate, vitamin C and derivatives thereof, DL-α-tocopherol, tocopherol E acetate, nicotinic acid, pantothenic acid and biotin. Vitamin E, which is often added to cosmetic products and personal care products is also preferably stabilized by the compounds according to the invention. Additional preferred vitamins are Vitamin C and K and derivatives thereof.

Furthermore, oils and waxes can also be stabilized by a compound of formula i, i', i", ii, ii', ii", iii, iii', iv and/or iv'. Both natural and synthetic oils and waxes can be stabilized. Natural waxes include, for example, carnauba wax, candelilla wax, rice bran wax, bees wax, lanolin, motan wax and ceresine wax. Synthetic waxes derived from hydrocarbons are, for example, paraffin wax, microcrystalline waxes, lauric acid, myristic acid, palmitic acid, stearic acid and behenic acid, sorbitane fatty acid esters and amides. Mixtures of waxes can also be stabilized. Natural oils include, for example, coconut oil, canola oil, soybean oil, rapeseed oil, palm kernel oil, murumuru tallow, and tucum oil.

As used herein, natural waxes and oils mean any wax or oil derived from plant or animal material including, but not limited to, waxes and oils that are derived from plants that have been genetically modified either through traditional breeding or through genetic engineering techniques.

The invention also relates to the stabilization of UV protectants/filters, for example, of ethylhexyl methoxycinnamate with the compounds of formula i, i', i", ii, ii', ii", iii, iii', iv and/or iv'.

The invention also includes household products themselves that contain at least one photosensitive poly-unsaturated or aromatic compound, which is either a color compound, a fragrance compound, a flavor compound, antioxidant or a combination of these compounds in combination at least one compound of formulae i, i', ii, ii', ii", iii, iii', iii", iv and/or iv', preferably i, i', ii, ii', iii, iii', iv and/or iv'. The household products are as described above protected from both visible and UV light, including from only visible light, or substantially or predominantly only from visible light, e.g., during storage, for example.

Household products are, for example, cleaning compositions, detergents, dishwashing liquids or powders, glass or furniture cleaning and/or polishing compositions, floor cleaning and/or polishing compositions, etc.

Poly-unsaturated color compounds which are not photochemically stable include, for example, carotenoids, Ubiquinones and Azulenes such as guaizulene. Guaiazulene has very limited photostability. Almost 90% of Guaiazulene is lost when exposed to solar simulator at a total energy of 100 $mJ/cm^2$. β-carotene, degrades in ambient light at room temperature storage.

Examples of photo-sensitive carotenoids include, for example, Lycopene, Zeaxanthine, Cantaxanthine, α-, β-, γ- & δ-Carotenes, Astacin, Astaxanthin, Chrysanthemaxanthin, Torularhodin, Violaxanthin, Capsanthin, Capsorubin and others.

Examples of photo-sensitive Azulenes, include, for example, Azulene, Guaiazulene, Guaiol and others.

Examples of photo-sensitive Ubiquinones (Coenzyme Q), include, for example, structures based on the 2,3-dimethoxy-5-methyl-benzoquinone nucleus with a variable terpenoid side chain containing one to twelve mono-unsaturated trans-isoprenoid units with ten units being the most common in animals. Compounds can be described as Coenzyme $Q_n$ in which n=1–12. Naturally occurring members are the Coenzymes $Q_6$–$Q_{10}$.

Examples of tocopherols are natural tocopherols. Tocopherols are a mixture of four lipid-soluble tocopherols (α, β, γ and δ) and four lipid-soluble tocotrienols (α, β, γ and δ). Tocopherols and tocotrienols differ only in their phenyl side chain. The chromanol head of each is identical with α, β, γ and δ-isomers, each containing an essential hydroxyl group necessary for antioxidant activity. Synthetic DL-Tocopherols or its derivatives, like acetate, succinate, etc. are also included. Photochemically, tocopherols (synthetic or natural) are not very stable (R K Chaudhuri, Phyllanthus tannins, in P Elsner and H I Maibach, eds. Cosmeceuticals: Drugs vs Cosmetics, New York, Marcel and Dekker, in press).

Included within the methods of this invention is the use of the compounds of formulae i, i', i", ii', ii", iii, iii', iv and/or iv' in stabilizing photosensitive dyes and/or organic pigments.

An example of photosensitive organic pigments that are stabilized by the compounds of formulae i, i', i", ii, ii', ii", iii, iii', iv and/or iv' are the curcuminoids. Curcuminoids are polyphenolic pigments found in the spice turmeric. Curcuminoids are responsible for the yellow color of turmeric, as well as the yellow color of curry. The major curcuminoids are curcumin, demethoxycurcumin and bisdemethoxycurcumin. These substances comprise 3 to 6% of *Curcuma longa*. Curcumin makes up 70 to 75% of the curcuminoids, demethoxycurcumin 15 to 20% and bisdemethoxycurcumin about 3%. *Curcuma longa* is a tropical plant native to south and southeast tropical Asia. It is a member of the ginger of Zingiberaceae family. Other Curcuminoids include Cassumunin A and Cassumunin B, isolated from tropical ginger, *Zingiber cassumunar*.

The term turmeric is used both for the plant *Curcuma longa L.* and the spice derived from the rhizomes of the plant. Turmeric is widely consumed in the countries of origin for a variety of uses, including use as a dietary spice, as a dietary pigment and as an Indian folk medicine for the treatment of various illnesses.

Fragrance ingredients are, for example: Abbarome 011®, Acalea, Allyl Amyl Glycolate, alpha-Terpineol, Alpha Pinene, Ambrettolide, Amyl Cinnamic Aldehyde, Amyl Phenyl Acetate, Amyl Salicylate, Andrane, Anethole 21/22, Anethole USP, Anethole USP, Aphermate, Apo Patchone, Bacdanol®, Benzyl n-Butyrate, Benzyl Propionate, Benzyl Salicylate, Bergamal, Beta Naphthyl Isobutyl Ether, Beta Pinene Coeur, Bicyclononalactone, Bornafix®, Canthoxal, Cashmeran®, Cedrafix, Cedramber®, Cedrenyl Acetate Chinese, Celestolide, Cinnamalva, cis-3-Hexenyl Salicylate, Citral Dimethyl Acetal, Citralva®, Citronalva, Citronellol 700 98TA, Citronellol 750, Citronellol 950, Citronellol Coeur, Citronellyl Acetate, Citronellyl Acetate A, Citronellyl Acetate Pure, Citronellyl Formate, Clarycet, Clonal, Coniferan, Cyclabute, Cyclacet™, Cyclaprop™, Cyclemone A, Cyclogalbaniff, Cyclohexyl Ethyl Acetate, Cyclohexyl Ethyl Alcohol, Damascol 4, Decyl Methyl Ether, Delta Damascone, Dihydro Cyclacet, Dihydro Floralate, Dihydro Floralol, Dihydro Myrcenyl Acetate, Dihydro Terpineol, Dihydro Terpinyl Acetate, Dihydro Terpinyl Acetate DSA, Dimethyl Benzyl Carbinol, Dimethyl Benzyl Carbinyl Acetate, Dimethyl Benzyl Carbinyl Butyrate, Dimethyl Cyclormol, Dimethyl Octanol-PQ, Dimethyl Phenyl Ethyl Carbinyl Acetate, Dimyrcetol, Diola, Dipentene 5100, Dulcinyl® Recrystallized, Ethyl 3 Phenyl Glycidate, Ethyl Ortho Methoxy Benzoate, Fleuramone, Fleuranil, Floralate, Floralol, Floralozone, Fraistone, Fructone, Galaxolide® 50 BB, Galaxolide® 50 DEP, Galaxolide® 50 DPG, Galaxolide® 50 IPM, Galbanum Coeur, Gelsone, Geraldehyde, Geraniol 5020, Geraniol 7030®, Geraniol 980, Geraniol Coeur, Geranyl Acetate, Geranyl Acetate Extra, Geranyl Acetate Pure, Grisalva, Guaiyl Acetate, Helional™, Herbac, Hexadecanolide, Hexalon, Hexyl Acetate, Hexyl Cinnamic Aldehyde, Hexyl Salicylate, Hyacinth Body, Hyacinth Body No. 3, Hydratropic Aldehyde Dimethyl Acetal, Hydroxyol, Hypo-Lem, Indolarome, Indolene 50, Intreleven Aldehyde, Intreleven Aldehyde Special, Ionone 100%, Ionone Alpha, Ionone Alpha Beta, Regular, Ionone Beta, Iso Amyl Butyrate, Iso Bornyl Propionate, Iso Butyl Quinoline, Iso E Super®, Isoamyl Salicylate, Isobutyl Phenyl Acetate, Isocyclemone E, Isocyclocitral, Isocyclogeraniol, Isoproxen, Jasmal, Jasmelia, Jessemal™, Kharismal, Koavone®, Kohinool®, Lavonax, Lemsyn, Liffarome, Lindenol®, Lymolene, Lyral®, Lyrame, Lyrame Super, Maritima, Melafleur, Methyl Anthranilate, Methyl Cedryl Ketone Chinese, Methyl Cinnamic Aldehyde alpha, Methyl Ionone Gamma A, Methyl Ionone Gamma Coeur, Methyl Ionone Gamma Pure, Methyl Lavender Ketone, Muguesia, Muguet Aldehyde 50, Muguet Aldehyde 50 BB, Myrac Aldehyde, Myrcenol Super, Myrcenyl Acetate, Neoproxen, Nerol 800, Nerol 850, Nerol 900, Neryl Acetate, Ocimene, Ocimenyl Acetate, Octacetal, Orange Flower Ether, Orivone, Orriniff 25% IPM, Oxaspirane, Ozofleur, Pamplefleur®, Peomosa, Phenafleur, Phenoxanol®, Phenoxyethyl Isobutyrate, Phenoxyethyl Propionate, Phenyl Ethyl Acetate, Phenyl Ethyl Alcohol, Phenyl Ethyl Benzoate, Phenyl Ethyl Formate, Phenyl Ethyl Isobutyrate, Phenyl Ethyl Phenyl Acetate, Phenyl Ethyl Salicylate, Piconia, Precyclemone B, Prenyl Acetate, Proflora, Pseudo Linalyl Acetate, Reseda Body, Rosalva, Rosamusk, Roseate, Rosemarel, Salicynalva, Sanjinol, Santaliff, Spirodecane, Strawberiff®, Styrallyl Propionate, Syvertal, Terpineol 900, Terpineol Extra, Terpinolene 20, Terpinolene 90, Terpinolene 90 PQ, Terpinyl Acetate (CST), Terpinyl Acetate (GUM), Tetrahydro Geraniol, Tetrahydro Muguol, Tetrahydro Muguol Coeur, Tetrahydro Myrcenol, Tetrameran, Tobacarol, Trimofix® O, Triplal™, Triplal™ Extra, Unipine 60®, Unipine 759, Unipine 80®, Unipine 85®, Unipine 90®, Unipine NCL®, Unipine S-70®, Unitene D®, Unitene LP®, Unitene WST®, Vandor B, Vanoris, Verdol, Verdox™, Verdox™ HC, Verdural B Extra, Verdural Extra, Vernol®, Vertenex®, Vertenex® HC, Vertofix® Coeur, Vigoflor, and Violiff.

Preferred fragrance ingredients are, for example, Muguet Aldehyde 50, Myrac Aldehyde, Phenyl Ethyl Formate, Precyclemone B, Syvertal, Strawberiff®, and Triplal™. The chemical formulae for these compounds, in the order listed across are:

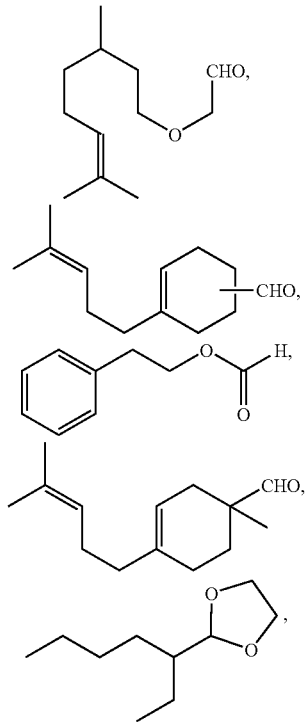

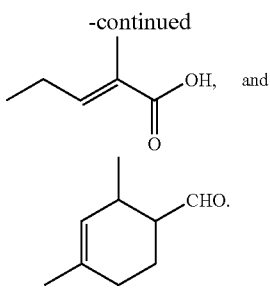

Flavor ingredients are, for example: 4,5-Dimethyl-2-ethyl-3-thiazoline, 6-Methyl Coumarin, Allyl Caproate, Anethole USP, Asafoetida Oil English Distilled SAS, Black Pepper, Black Pepper, Black Pepper Oil, Black Pepper Oil English Distilled SAS, Buchu Sulfur Fractions, Butyric Acid, Cardamon Oil English Distilled SAS, Cassia Oil, Cassia Oil Redistilled, Cinnamon Bark Oil, Cinnamon Leaf Oil Cleaned, Clove Bud Oil English Distilled SAS, Clove Leaf Oil Cleaned, Clove Leaf Oil Redistilled, Cocal™, Cocoa Distillate (Nat.), Cocoa Essence Dark, Cocoa Essence White, Cocoa Extract Nat., Coffee Enhancer Base, Coffee Enhancer W/S, Coffee Extract, Coffee Extract Italian Roast M3881 Nat., Coffee Extract Nce Iiim Nat., Coffee Extract Nce Iv Nat., Coriander Oil, Cyclodithalfarol-705, delta Decalactone, Dimethyl Benzyl Carbinyl Butyrate, Dimethyl Sulfide, Dithione 865, Ethyl-2-Methyl Butyrate, Ethyl-3-Hydroxy Butyrate, Ethyl Butyrate, Ethyl Iso Butyrate, Ethyl Iso Valerate, Ethyl Oxanoate 369, Eucalyptus Oil 80%, Farnesene 1% PG/ETOH, Furfurrole 302, gamma-Decalactone, gamma-Hexalactone, gamma-Octalactone, gamma Dodecalactone, Ginger Oil Chinese, Ginger Oil Nigerian English Distilled SAS, Grapefruit Key, Grill Flavor O/S, Grill Flavor W/D, Heptan-2-One (Nat.), Hexene-3-One-4, Hexyl Acetate, Homo Cyclocitral, beta, Honey Distillate Nat., Ionone Beta, Iso Amyl Iso Valerate, Iso Butyl Caproate, Iso Fragarone-030, Iso Fragarone, 1% ETOH™, Isobutyl Furyl Propionate, Isovaleric Acid, Juniperberry Oil English Distilled SAS, Ketone Mix, Kumarone™, Lemon Oil 5×Sas, Lemon Oil Terpeneless Sas, Lemonless Lemon Key, Lime Oil Terpeneless, Linalool 75/80% Ex Orange (Nat.), Linalyl Acetate (Nat.), Mangone 5% ETOH™, Methional, Methyl Butyric Acid (2), Methyl Ketones (Nat.), Methyl Oxycyclosulfide 719, Mushroom Extract, Natural Flavor (99% Vanillin), Nat. Cocoa Butter Distillate, Nat. Peanut Distillate, Nonan-2-One (Nat.), Nutmeg Oil East Indian, Octanal 35% (Nat.), Octen-4-one-2, Olibanum Oil English Distilled SAS, Orange Oil 15× Decolorized M3706, Orange Oil 950 (10×), Orange Oil Terpeneless 2501, Oxaromate-884, Oxycyclothione-030, Paradiff™ 0.01% ETO-HGR, Paradiff™ 0.01% Grapefruit Oil, Peach Flavor Key, Peppermint Oil Redistilled Yakima, Peppermint Oil Spec. Fractions, Phenyl Ethyl 2-Methyl Butyrate, Phenyl Ethyl Acetate, Phenyl Ethyl Alcohol, Phenyl Ethyl Isovalerate, Phenyl Oxaromate-681, Pimento Berry Oil English Distilled SAS, Pimento Leaf Oil, Pimento Leaf Oil Cleaned, Pineapple Compound 15% ETOH GR, Pineapple Compound 15% PG, Popcorn Chemical, Propionic Acid, Raspberry Flavor Key, Raspberry Flavor Key, Raspberry Flavor Key, Robustone 1.0% ETOH™, Robustone™, Schinus Molle Oil, Sclareolide, Sesame Distillate Nat., Sinensals (Nat.), Spearmint Oil Terpeneless, Starter Distillate 15×W/S, Strawberriff, Strawberry Base, Strawberry Flavor Key, Strawberry Flavor Key, Succinic Acid, Sulfurome-015, Sweetness Modifier, Tetrahydro Terrazine-014™, Thionol-935, Thionol-966, trans-2-Hexenal, Trimenal Acetate 399 1% ETOH™, Tropical Fruit Key Base, Tropical Fruit Key Base, Undecan-2-One (Nat.), Varamol-106 10% ETOH, Varamol-106 10% NEBM5, and Varamol-106 10% PG.

Preferred flavor ingredients are, for example, Methional, whose chemical formula is

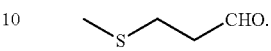

Essential oils can also be photostabilized by the compounds of the invention. The *INCI Dictionary* includes more than 100 essential oils. Only a few of them are mentioned here: Basil, Bergamot, Black Pepper, Cedarwood, Chamomile, Cinnamon, Clary Sage, Clove, Coriander, Cypress, Eucalyptus, Fennel, Geranium, Ginger, Grapefruit, Jasmine, Juniper, Lavender, Lemon, Lemongrass, Melaleuca or Tea Tree, Myrrh, Olibanum, Patchouli, Peppermint, Rose, Rosemary, Rosewood, Sage, Sandalwood, and Thyme.

Essential oils can be obtained, for example, by compression or solvent extraction. In an alternate process, odoriferous plant parts are steam distilled. The oil may then be collected by separation from the condensed distillate. The leftover water distillate contains plant components and some volatile oils. This material is normally marketed as a water. Typical flower representatives are cabbage rose (*Rosa centifolia*) flower water, matricaria water, and peppermint leaf water. A similar distillate is obtained from *Hamamelis virginiana* but is marketed primarily as a hydroalcoholic solution.

Natural colors, compounds responsible for the coloration of plants, etc., appearing in nature, e.g., extracts thereof or synthetic versions thereof, can also be stabilized, i.e., protected from photodegradation, by the compounds of the invention, which compounds are generally unstable.

Certain pigments, for example, Annatto (Bixin), Anthocyanin, Beta-carotene, Betanin, Capsanthin/capsorubin, Chlorophyll, Crocetin, Curcumin, and Luteolin, can also be photostabilized by the compounds of the invention.

Bioflavonoids and flavonoids can also be photostabilized by the compounds of the invention. These compounds belong to a large series of plant-derived phenolics. Some of these compounds are deeply colored and may be used for their tinctorial attributes. Some members of this group impart color. Compounds belonging to this group of compounds, are, for example, Alizarin, Purpurin, Amaranth, Annatto, Anthocyanidins, Apigenin, Azulene, Betalaines and Betanines, phytolaccanin, (Blue) Gardenia, Caramel, Carotenes, Lycopene, Canthaxathin, Capsanthin/Capsorubin, Xanthophyll, Carthamin, Chlorophyll, Crocin and Crocetin, crocetin, Curcumin, desmethoxycurcumin, Indigo, Juglone, Lawsone, Luteolin, Phycocyanobilin, Pratol, Santalin, Shikonin, and alkannin.

Certain inorganic compounds also photodegrade, and can be stabilized against this degradation by the compounds of this invention. Some exemplary inorganic compounds are: iron oxides, which may be represented by the general formulas as follows: Yellow Oxide $Fe_2O_3$—$H_2O$. Red Oxide, being the anhydrous form of Yellow Oxide, is $Fe_2O_3$. Black Oxide is $FeO$—$Fe_2O_3$; Ferric ammonium ferrocyanide may be represented as $Fe(NH_4)Fe(CN)_6.nH_2O$; Manganese violet, a manganese ammonium pyrophosphate complex, may be represented as $Mn(NH_4)P_2O_7$; Ultramarine blue is a complex sodium aluminum sulfo-silicate having the approximate formula $Na_7Al_6O_{24}S_3$. The intense color is the result of the polysulfide linkage, which is present in a highly resonant state; Chrome oxide green, is a chromium sesquioxide $Cr_2O_3$, whereas hydrated chromium sesquioxide is principally $Cr_2O_3 \cdot nH_2O$.

Some organic colors can also be photostabilized by the methods of this invention. For example, reds (D&C Red #6 Barium Lake, D&C Red #6, D&C Red #7, D&C Red #21, D&C Red #22, D&C Red #27, D&C Red #28, D&C Red #30, D&C Red #33 Aluminum Lake, D&C Red #34 Calcium Lake, D&C Red #36, and FD&C Red #40 Aluminum Lake), orange (D&C Orange #5), yellows (FD&C Yellow #5 Aluminum Lake, FD&C Yellow #6 Aluminum Lake, FD&C Yellow #10 Aluminum Lake), and blue (FD&C Blue#1 Aluminum Lake).

A listing of approved colorants (except hair colors) that can be stabilized by the compounds of the invention are found in U.S. Food and Drug Administration color additive regulations, 21 CFR 73 and 74. A listing of colorants in EU Member States may be found in Annex IV of the EC Cosmetics Directive 76/768/EEC.

Some colorants are, for example, Acid Black 1, Acid Black 52, Acid Blue 3, Acid Blue 9, Acid Blue 9 Aluminum Lake, Aka223, Chromium Oxide Greens, Acid Blue 9 Ammonium Salt, Acid Blue 62, Acid Blue 74, Acid Blue 74 Aluminum Lake, Acid Green 1, Acid Green 25, Acid Green 50, Acid Orange 6, Acid Orange 7, Acid Red 14 Aluminum Lake, Acid Red 18, Acid Red 18 Aluminum Lake, Acid Red 27, Acid Red 27 Aluminum Lake, Acid Red 33, Acid Red 51, Acid Red 73, Acid Red 87, Acid Red 92, Acid Red 95, Acid Red 184, Acid Red 195, Acid Violet 9, Acid Violet 43, Acid Yellow 3, Acid Yellow 3 Aluminum Lake, Acid Yellow 23, Acid Yellow 23 Aluminum Lake, Acid Yellow 73, Basic Blue 6, Acid Yellow 73 Sodium Salt, Acrylic Resin Coated Aluminum Powder, Aka2, Aka3, Aka102, Aka104(1), Aka105(1), Aka106, Aka201, Aka202, Aka203, Aka204, Aka205, Aka206, Aka207, Aka208, Aka213, Aka214, Aka215, Aka218, Aka219, Aka220, Aka221, Aka22, Aka225, Aka226, Aka227, Aka228, Aka230(1), Aka230(2), Aka231, Aka232, Aka401, Aka404, Aka405, Aka501, Aka502, Aka503, Aka504, Aka505, Aluminum Laccate, Aluminum Powder, Aluminum Stearate, Annatto, Anthocyanins, Ao1, Ao2, Ao201, Ao202, Ao203, Ao204, Ao205, Ao403, Ao404, Astaxanthin, Basic Blue 6, Basic Blue 41, Basic Yellow 11, Beetroot, Bismuth Oxychloride, Blue 1, Blue 1 Lake, Blue 4, Brilliant Black 1, Bromocresol Green, Bromothymol Blue, Bronze Powder, Brown 1, Calcium Ferrite, Calcium Stearate, Capsanthin/Capsorubin, Caramel, Carbon Black, Carmine, Beta-Carotene, Carotenolds, Chlorophyllin-Copper Complex, Chromium, Chromium Hydroxide Green, Cl 10006, Cl 10020, Cl 10316, Cl 11680, Cl 11710, Cl 11725, Cl 11920, Cl 12010, Cl 12085, Cl 12120, Cl 12150, Cl 12370, Cl 12420, Cl 12480, Cl 12490, Cl 12700, Cl 13015, Cl 14270, Cl 14700, Cl 14720, Cl 14815, Cl 15510, Cl 15525, Cl 15580, Cl 15620, Cl 15630, Cl 15800, Cl 15850, Cl 15865, Cl 15880, Cl 15980, Cl 15985, Cl 16035, Cl 16185, Cl 16230, Cl 16255, Cl 16290, Cl 17200, Cl 18050, Cl 18130, Cl 18690, Cl 18736, Cl 18820, Cl 18965, Cl 19140, Cl 20040, Cl 20170, Cl 20470, Cl 21100, Cl 21108, Cl 21230, Cl 24790, Cl 26100, Cl 27290, Cl 27755, Cl 28440, Cl 40215, Cl 40800, Cl 40820, Cl 40825, Cl 40850, Cl 42045, Cl 42051, Cl 42053, Cl 42080, Cl 42090, Cl 42100, Cl 42170, Cl 42510, Cl 42520, Cl 42735, Cl 44045, Cl 44090, Cl 45100, Cl 45190, Cl 45220, Cl 45350, Cl 45370, Cl 45380, Cl 45396, Cl 45405, Cl 45410, Cl 45425, Cl 45430, Cl 47000, Cl 47005, Cl 50325, Cl 50420, Cl 51319, Cl 58000, Cl 59040, Cl 60724, Cl 60725, Cl 60730, Cl 61565, Cl 61570, Cl 61585, Cl 62045, Cl 69800, Cl 69825, Cl 71105, Cl 73000, Cl 73015, Cl 73360, Cl 73385, Cl 73900, Cl 73915, Cl 74100, Cl 74160, Cl 74180, Cl 74260, Cl 75100, Cl 75120, Cl 75125, Cl 75130, Cl 75135, Cl 75170, Cl 75300, Cl 75470, Cl 75810, Cl 77000, Cl 77002, Cl 77004, Cl 77007, Cl 77015, Cl 77120, Cl 77163, Cl 77220, Cl 77231, Cl 77266, Cl 77267, Cl 77268:1, Cl 77288, Cl 77289, Cl 77346, Cl 77400, Cl 77480, Cl 77489, Cl 77491, Cl 77492, Cl 77499, Cl 77510, Cl 77713, Cl 77742, Cl 77745, Cl 77820, Cl 77891, Cl 77947, Cobalt Aluminum Oxide, Cochineal, Copper Powder, Crocus Sativus Flower Extract, Curry Red, Daidai201, Daidai203, Daidai204, Daidai205, Daidai206, Daidai207, Daidai401, Daidai402, Daidai403, Dihydroxyacetone, Direct BLue 86, Disodium EDTA-Copper, Dunaliella Bardawil Powder, Epoxy Resin Coated Aluminum Powder, Erythrulose, Ext. Violet 2, Ext. Yellow 7, Ext. Yellow 7 Lake, Fast Green FCF, Ferric Ammonium Citrate, Ferric Ammonium Ferrocyanide, Ferric Ferrocyanide, Fluorescent Brightener 230, Fluorescent Brightener 236, Gardenia Florida Extract, Gold, Green 3, Green 3 Lake, Green 5, Green 6, Green 8, ne, Guanine, Haematococcus Pluvialis Powder, Haematoxylon Campechianum Wood Extract, Henna, Iron Oxides, Katsu201, Ki4, Ki5, Ki201, Ki202(1), Ki202(2), Ki203, Ki204, Ki205, Ki401, Ki402, Ki403(1), Ki404, Ki405, Ki406, Ki407, Kuro401, Lactoflavin, Lawsone, Magnesium Stearate, Manganesa Violet, Mica, Midori3, Midori201, Midori202, Midori204,k Midori205, Midori401, Midori402, Murasaki201, Murasaki401, Natural Red 26, Ninhydrin, Orange 4, Orange 4 Lake, Orange 5, Orange 5 Lake, Orange 10, Orange 10 Lake, Orange 11, Oxobenzoxazinyl Naphthalene Sulfoanilide, Pigment Blue 15:2, Pigment Green 7, Pigment Orange 5, Pigment Red 4, Pigment Red 5, Pigment Red 48, Pigment Red 53, Pigment Red 53:1, Pigment Red 57, Pigment Red 57:1, Pigment Red 63:1, Pigment Red 64:1, Pigment Red 68, Pigment Red 83, Pigment Red 88, Pigment Red 90:1 Aluminum Lake, Pigment Red 112, Pigment Red 172 Aluminum Lake, Pigment Red 173 Aluminum Lake, Pigment Red 190, Pigment Violet 19, Pigment Yellow 1, Pigment Yellow 3, Pigment Yellow 12, Pigment Yellow 73, Ponceau SX, Pyrophyllite, Red 4, Red 4 Lake, Red 6, Red 6 Lake, Red 7, Red 7 Lake, Red 17, Red 21, Red 21 Lake, Red 22, Red 22 Lake, Red 27, Red 27 Lake, Red 28, Red 28 Lake, Red 30, Red 30 Lake, Red 31, Red 31 Lake, Red 33, Red 33 Lake, Red 34, Red 34 Lake, Red 36, Red 36 Lake, Red 40, Red 40 Lake, Silver, Sodium 5-Nitroguaiacolate, Sodium Zinc Cetyl Phosphate, Solvent Green 3, Solvent Green 7, Solvent Orange 1, Solvent Red 1, Solvent Red 3, Solvent Red 23, Solvent Red 24, Solvent Red 43, Solvent Red 48, Solvent Red 49:1, Solvent Red 72, Solvent Red 73, Solvent Violet 13, Solvent Yellow 18, Solvent Yellow 29, Solvent Yellow 33, Solvent Yellow 44, Sunset Yellow, Sunset Yellow Aluminum Lake, Titanium Dioxide, Titanium Oxynitride, Titanium/Titanium Dioxide, Ultramarines, Umber, Vat Red 1, Violet 2, Yellow 5, Yellow 5 Lake, Yellow 6, Yellow 6 Lake, Yellow 7, Yellow 7 Lake, Yellow 8, Yellow 10, Yellow 10 Lake, Yellow 11, Yellow Ocher, Zinc Oxide, Zinc Stearate.

In other aspects, the invention is directed to compositions containing compounds of formulae i, i', i'', ii, ii', ii'', iii, iii', iv and/or iv' and certain poly-unsaturated color and aromatic compounds, dyes, organic pigments, antioxidants, fragrance compounds or flavor compounds. These compositions can be in the form of a complete retail cosmetic, personal care, or household products or an intermediate to a complete retail product. Therefore, the compositions of this invention may optionally contain one or more carriers or solubilizers used in cosmetics, personal care or household products, for example, esters of long-chain fatty acids or short or long chain alcohols.

Amounts of the compounds of formulae i, i', i", ii, ii', ii", iii, iii', iv and/or iv' within such compositions typically range from 0.1 to 40 wt % based on the total weight of the composition. More typically, the amount falls within the range of 1 wt % to 25 wt %, even more preferably ranges from about 2 wt % to about 15 wt %. Typical ratios of stabilizer to color, or antioxidant, or flavor or fragrances are 1:1 to 1:10, preferably between 1:1 to 1:5.

As used herein and in the claims, when "a" compound or class of compounds is named, or "at least a" or "at least one" compound or class of compounds is named, it is understood that "one or more" is meant and intended, for example, from each class of compounds named.

Additional ingredients that can be used in the compositions of this invention are organic sunscreen agents, metal oxide sunscreen agents, dispersing agents, preservatives, anti-foams, perfumes, oils, waxes, propellants, dyes, pigment emulsifiers, surfactants, thickeners, humectants, exfoliants and emollients. These compositions may be in the form of a cosmetic composition with a cosmetically acceptable carrier and one or more cosmetic adjuvants. The compositions can optionally have antioxidants or other stabilizers which do not have UV absorbing characteristics.

The methods of using the complete retail products that are the compositions of the invention comprise applying said composition to a substrate, for example, skin, hair, leather, fabrics, for example, clothing articles, wigs, etc. Preferred substrates are skin and hair.

The compositions of this invention may contain dispersing agents, emulsifiers or thickening agents to assist in applying a uniform layer of the active compounds. Suitable dispersing agents for the composition include those useful for dispersing organic or inorganic sunscreen agents in either a water phase, oil phase, or part of an emulsion, including, for example, chitosan.

Emulsifiers may be used in the compositions, for example, sunscreen formulations, to disperse one or more of the compounds of formulae i, i', i", ii, ii', ii", iii, iii', iv and/or iv' or other component of the composition. Suitable emulsifiers include agents such as, for example, glycerol stearate, stearyl alcohol, cetyl alcohol, dimethicone copolyol phosphate, hexadecyl-D-glucoside, octadecyl-D-glucoside, etc.

Thickening agents may be used to increase the viscosity of the compositions. Suitable thickening agents include carbomers, acrylate/acrylonitrile copolymers, xanthan gum and combinations of these. The carbomer thickeners include the crosslinked CARBOPOL® acrylic polymers from B.F. Goodrich. The amount of thickener within the composition, for example, a sunscreen formulation, on a solids basis without water, may range from about 0.001 to about 5%, preferably from 0.01 to about 1% and optimally from about 0.1 to about 0.5% by weight.

Minor optional adjunct ingredients for the compositions may include preservatives, waterproofing agents, fragrances, anti-foam agents, plant extracts (Aloe vera, witch hazel, cucumber, etc) opacifiers, skin conditioning agents and colorants, each in amounts effective to accomplish their respective functions.

The compositions may optionally contain an ingredient which enhances the waterproof properties such as, compounds that form a polymeric film, such as dimethicone copolyol phosphate, diisostearoyl trimethyolpropane siloxysilicate, chitosan, dimethicone, polyethylene, polyvinylpyrrolidone (PVP), polyvinylpyrrolidone/vinylacetate, PVP/Eiconsene copolymer and adipic acids/diethylene glycol/glycerine crosspolymer etc. Waterproofing agents may be present at levels of from about 0.01 to about 10% by weight.

The compositions, may also optionally contain one or more skin conditioning agents. These include humectants, exfoliants and emollients.

Humectants are polyhydric alcohols intended for moisturizing, reducing scaling and stimulating the removal of built scale from the skin. Typically polyhydric alcohols include polyalkylene glycols and more preferably alkylene polyols and their derivatives. Illustrative are propylene glycol, dipropylene glycol, polypropylene glycol, polyethylene glycol, sorbitol, 2-pyrrolidone-5-carboxylate, hydroxypropyl sorbitol, hexylene glycol, ethoxydiglycol 1,3-butylene glycol, 1,2,6-hexanetriol, glycerin, ethoxylated glycerin, propoxylated glycerin and mixtures thereof. Most preferably the humectant is glycerin. Amounts of humectant can range anywhere from 1 to 30%, preferably from 2 to 20% and optimally from about 5 to 10% by weight of the composition.

The exfoliants suitable for use in the present may be selected from alpha-hydroxy carboxylic acids, beta hydroxycarboxylic acids and salts of these acids. Most preferred are glycolic, lactic and salicylic acids and their alkali, metal or ammonium salts.

Suitable emollients include those agents known for softening the skin or hair which may be selected from hydrocarbons, fatty acids, fatty alcohols and esters. Petrolatum is a common hydrocarbon type of emollient conditioning agent. Other hydrocarbons that may be employed include alkyl benzoate, mineral oil, polyolefins such as polydecene, and paraffins, such as isohexadecane. Fatty acids and alcohols typically have from about 10 to 30 carbon atoms. Illustrative are myristic, isostearic, hydroxystearic, oleic, linoleic, ricinoleic, behenic and eruicic acids and alcohols. Oily ester emollients may be those selected from one or more of the following, triglyceride esters, acetoglyceride esters, ethoxylated glycerides, alkyl esters of fatty acids, ether esters, polyhydric alcohol esters and wax esters. Additional emollients or hydrophobic agents include $C_{12}$ to $C_{15}$ alkyl benzoate, dioctyladipate, octyl stearate, octyldodecanol, hexyl laurate, octyldodecyl neopentanoate, cyclomethicone, dicapryl ether, dimethicone, phenyl trimethicone, isopropyl myristate, capriylic/capric glycerides, propylene glycol dicaprylate/dicaprate and decyl oleate, isopropyl citrate, diisopropyl adipate, ethylhexyl neopentanoate, isopropyl laurate, hexyl laurate, $C_{12-15}$ alkyl benzoate, ethylhexyl palmitate, octyldodecyl neopentatnoate, ethylhexyl state etc.

Examples of esters of long-chain fatty acids, for example, include: long-chain fatty acid esters of retinol; long-chain fatty acid ester of ascorbic acid; long-chain fatty acid ester of glycerol; etc. The long-chain fatty acid ester of retinol can be selected from the group consisting of retinyl palmitate, retinyl myristate, and retinyl stearate. Most preferably, the retinyl ester is retinyl palmitate. Preferably, the retinyl ester comprises from about 0.05% to about 0.15% of a skin cream composition. The long-chain fatty acid ester of ascorbate can be selected from the group consisting of ascorbyl myristate, ascorbyl palmitate, and ascorbyl stearate. Preferably, the ascorbic acid ester is ascorbyl palmitate. Preferably, the ascorbic acid ester comprises from about 0.01% to about 0.02 to 0.03% of the composition.

The long-chain fatty acid ester of glycerol can be selected from the group consisting of glyceryl stearate, glyceryl palmitate, and glyceryl arachidate. Preferably, the ester of glycerol is glyceryl stearate. Preferably, the glyceryl stearate comprises from 0.5% to about 0.7% of the composition.

Examples of short or long chain alcohols, for example, include: hexyl (chain-length, C-6), caprylyl (C-8), decyl (C-10), lauryl (C-12), myristyl (C-14), cetyl (C-16), stearyl (C-18), arachidyl (C-20), behenyl alcohols (C-22).

The compositions may optionally contain one or more inorganic sunscreen agents as discussed above including micro fine surface treated titanium dioxide and micro fine untreated and surface treated zinc oxide. Titanium dioxide in the compositions preferably has a mean primary particle size of between 5 and 150 nm and preferably from 10 to 100 nm. Titanium oxide may have anatase, rutile or amorphous structure. The zinc oxide in the sunscreen compositions preferably has a mean primary particle size of between 5 nm and 150 nm, preferably between 10 nm and 100 nm. Examples of modified titanium dioxide compositions include:

Eusolex® T-45D (surface treated with alumina and simethicone, 45% dispersion in isononoyl isononoate);

Eusolex® T-Aqua, (surface treated with aluminum hydroxide, 25% dispersion in water); and Eusolex® T-2000 (surface treated with alumina and simethicone), Eusolex® TS (surface treated with aluminum stearate), and Eusolex® T-AVO (surface treated with silica), all available from MERCK KGaA.

Particularly useful organic sunscreen agents that can be introduced are Avobenzone, 2-ethylhexyl p-methoxycinnamate, 4,4'-t-butylmethoxydibenzoyl methane, 2 hydroxy-4-methoxybenzophenone, octyldimethyl p-aminobenzoic acid, 2,2-dihydroxy-4-methoxybenzophenone, ethyl-4-[bis(hydroxypropyl)]aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid, 2-ethylhexyl p-dimethylaminobenzoate, 2-phenylbenzimidazole-5-5-sulfonic acid, 2-(p-dimethylamino phenyl-5-sulfoniobenzoxazoic acid and mixtures thereof.

Examples of useful commercially available organic sunscreen agents that can be introduced include 2-phenylbenzimidazole-5-sulphonic acid, 2-(4-methylbenzylidene)-camphor, 4-isopropyldibenzoyl methane all of the Eusolex™ series sold by EMD Chemicals and Merck KGaA, Darmstadt, Germany.

The compositions may also contain one or more additional monomeric organic chromophoric compounds. These can either be UV-A, UV-B or broad band filters. Examples of suitable UV-A sunscreens include benzophenone derivatives, menthyl anthranilate, butyl methoxydibenzoyl methane and benzylidene-dioxoimidazoline derivatives. Examples of suitable UV-B sunscreens include cinnamate derivatives, salicylate derivatives, para-aminobenzoic acid derivatives, camphor derivatives, phenylbenzimidazole derivatives and diphenylacrylate derivatives. Examples of suitable broad-band sunscreen include benzotriazole derivatives and triazine derivatives such as anisotriazone. Others include ethylhexyltriazone and diethylhexylbutamidotriazone.

The compounds of formulae i, i', i", ii, ii', ii", iii, iii', iv and/or iv' can be introduced into a skin care formulation, a hair care formulation or other personal care formulations such as cosmetic formulations at levels which provide antioxidant activity.

Although not preferred, the compositions may contain an additional conventional antioxidant. Examples of suitable antioxidants which provide stability include p-hydroxybenzoic acid and its derivatives (ethylisobutyl, glyceryl esters of p-hydroxybenzoic acid); salicylates (octylamyl, phenyl, benzyl menthyl, glycerol and dipropyleneglycol esters); coumarin derivatives; flavones; hydroxy or methoxy substituted benzophenones; uric or tannic acid and its derivatives; and benzophenones. Also, the compositions may contain natural antioxidants, such as, Emblica antioxidant, Pine antioxidant, Grape antioxidant, Green tea antioxidant and others. The compounds of formulae i, i', i", ii, ii', ii", iii, iii', iv and/or iv' can be used to protect conventional antioxidants from photodegradation in personal care formulations such as hair care, skin care and cosmetic formulations.

The personal care and cosmetics formulations can be in the form of creams, ointments, suspensions, powders, oil, lotions, oleo alcoholic lotions, fatty gels, oleo-alcoholic gels and lotions, solid sticks, foams, emulsions, liquid dispersions, sprays and aerosols. More specific forms include: lotions, lipsticks, foundations, makeup, loose or press powder, eye blush, eye shadow, shampoo, conditioner and nail lacquer. The household formulations can be in the form of solids sticks, solutions, sprays, foams, liquid dispersions, or loose powders.

The entire disclosure of all applications, patents and publications, cited above are hereby incorporated by reference. All percentages are by weight.

BRIEF DESCRIPTION OF THE DRAWINGS

FIG. 1 shows color change of Vanillin (van.) in solution under sun simulator with and without Diethyhexyl syringylidene malonate (ST) in solution. (Dosage in MED)

FIG. 2 shows color change of Menthyl anthranilate (M. anthr.) under sun simulator with and Diethyhexyl syringylidene malonate (ST) in solution. (Dosage in MED)

FIG. 3 shows singlet oxygen scavenging properties of compounds of present invention (Eusolex HP=Bis-N[3'-(N,N dimethylamino)propyl]-3,5-dimethoxy-4 hydroxybenzylidene malonamide bis ethyl sulfate; Oxynex ST=Diethyhexyl syringylidene malonate, Eusolex ASA=Isoamyl alpha aceryl-3,5 dimethoxy 4 hydroxy benzylidene malonate) and Vitamin E and Ascorbic Acid.

EXPERIMENTAL

Example 1

Methodology

1. Test Methods for Photostabilization Studies

In Solution: Solutions in ethanol are prepared at respective concentrations of photosensitive materials and photostabilizer (typically 1:1 to 1:5 in weight %). Solutions are exposed to a sun simulator (754 W/m$^2$, 2 MED/h,) for various durations and light absorption spectra recorded for each sample at given times. The amount of photosensitive materials remaining in solution is calculated from the ratio of their maximal absorption band ($\lambda$max), before and after irradiation.

In Formulation: Samples are prepared as ultrathin films between two quartz plates as to obtain a minimum of 90% light transmission over the entire spectrum range of non absorbing chromophores. For example, ingredients which absorb only in the UV will be tested in formulation to obtain a minimum of 90% light transmission over the visible range. Samples are then irradiated under sun simulator (754 W/m$^2$, typically 2 MED/h) for given times and light absorption spectra recorded at each time. The remaining percentage of photosensitive compounds is calculated from the light absorption maximum ($\lambda$max) of the corresponding peak in the absorption spectrum.

Amount of energy: 10 mJoules/Cm$^2$=1 MED

Example 2

Photostabilization Results of Guaiazulene in Ethanolic Solution

| Sample Description | Relative absorption of Guaiazulene at 600 nm (%) | | | |
|---|---|---|---|---|
| | 0 MED | 2 MED | 5 MED | 10 MED |
| Guaiazulene (0.01%) | 100 | 83 | 43 | 6 |
| Guaiazulene + Diethylhexyl syringylidene malonate (0.01%:0.02%) | 100 | 97 | 90 | 70 |
| Guaiazulene + Diethylhexyl syringylidene malonate (0.01%:0.05%) | 100 | 98 | 95 | 85 |
| Guaiazulene + Diethylhexyl syringylidene malonate (0.01%:0.10%) | 100 | 99 | 96 | 87 |
| Guaiazulene + isoamyl-alpha-acetyl-3,5,-dimethoxy-4-hydroxy benzylidene malonate (0.02%:0.10%) | 100 | 97 | 90 | 80 |

Example 3

Photostabilization Results of Vanillin in Ethanolic Solution

| Sample Description | Relative absorption of Vanillin at 281 nm (%) | | | |
|---|---|---|---|---|
| | 0 MED | 2 MED | 5 MED | 10 MED |
| Vanillin (0.1%) | 100 | 45 | 40 | 36 |
| Vanillin + Diethylhexyl syringylidene malonate (0.1%:0.5%) | 100 | 96 | 92 | 83 |

Example 3A

Color Change of Vanillin in Solution Under Sun Simulator With and Without Diethylhexyl Syringylidene Malorate in Solution The result are demonstrated in FIG. 1. Without Diethylhexyl syringylidene malonate, a new light absorption band appears around 390 nm (responsible for a yellow color) which does not appear in the presence of Diethylhexyl syringylidene malonate.

Example 3B

Photostabilization Results of Vanillin in Ethanolic Solution with isoamyl-alpha-acetyl-3,5-dimethoxy-4-hydroxy cinnamate This study was repeated as described in the Experiment 3A and found to provide similar stabilization to vanillin when compared to the control (without stabilizer).

Example 4

Color Change of Menthyl Anthranilate Under Sun Simulator With and Without Diethylhexyl Syringylidene Malonate in Solution The result are demonstrated in FIG. 2. Similar to Vanillin, a new light absorption band for menthyl antranillate appears around 390 nm (responsible for a yellow color) in the absence of Diethylhexyl syringylidene malonate. The presence of Diethylhexyl syringylidene malonate (ratio of menthyl anthralinate: stabilizer/1:5) prevents any alteration/degradation of the fragrance.

Example 5

Photostability of Guaiazulene in a Shampoo Formulation, With and Without a Photostabilizer

| Sample Description | Relative absorption of Guaiazulene at 600 nm (%) | | | |
|---|---|---|---|---|
| | 0 MED | 2 MED | 5 MED | 10 MED |
| Guaiazulene (0.02%) in Shampoo | 100 | 82 | 49 | 11 |
| Guaiazulene + Diethylhexyl syringylidene malonate - (0.02%:0.1%) | 100 | 96 | 88 | 62 |

Result: Inclusion of Diethylhexyl syringylidene malonate (0.1%) in the shampoo shows a clear improvement in the photostability of Guaiazulene under sun simulator.

Formulation Used for the Study Described in Example-5

| INCI name | Trade Name/Supplier | % w/w | % w/w |
|---|---|---|---|
| Phase A-1 | | | |
| Water (demineralized) | | 60.25 | 60.25 |
| Propylene Glycol | | 1.00 | 1.00 |
| Polyquaternium-10 | U-Care Polymer JR-400/Amerchol | 0.20 | 0.20 |
| Disodium EDTA | | 0.10 | 0.10 |
| Phase B | | | |
| Sodium Laureth Sulfate | Standapol ES-1/Cognis | 30.00 | 30.00 |
| Lauryl Glucoside | Plantaren 1200N/Cognis | 4.00 | 4.00 |
| Cocoamidopropyl Betaine | Velvetex BA-35 | 7.50 | 7.50 |
| Phase C | | | |
| Guaiazulene | Rona | 0.01 | 0.01 |
| Phase D | | | |
| Diethylhexyl syringylidene malonate | Oxynex ST/Rona | 0.10 | |
| Polysorbate 20 | Tween 20/Uniqema | 0.05 | 0.05 |
| Peg-45 Palm Kernel Glycerides | Crovol PK-70/Croda | 0.10 | 0.10 |
| Phase E | | | |
| Methylchloroisothiazolinone, Methylisothiazolinone | Kathon CG/Rohm Haas | 0.06 | 0.06 |

-continued

| INCI name | Trade Name/Supplier | % w/w | % w/w |
|---|---|---|---|
| Phase F | | | |
| Sodium Chloride 20% sol | | 2.00 | 2.00 |
| Citric Acid | Adjust pH to 6.5–7.0 | 0.00 | 0.00 |
| Total | | 100.00 | 100.00 |

Procedure: Combine A and heat to 70–75° C., except for U-care JR-400. Disperse U-care JR-400 in A under agitation. Add ingredients of phase B one by one at 70° C. Add phase C at 40° C. Premix Phase D and add to batch at 40° C. At 35° C. add phase E. Adjust pH (~6.5) and viscosity with phase F.

Example 6

Photostability of Ubiquinone Under Sun Simulator in a Lotion, With and Without Diethylhexyl Syringylidene Malonate as a Photostabilizer at Different Weight Ratios to Ubiquinone

| Sample Description | Relative absorption of Ubiquinone at 275 nm (%) | | | |
|---|---|---|---|---|
| | 0 MED | 2 MED | 5 MED | 10 MED |
| Ubiquinone (0.2%) in a lotion | 100 | 71 | 65 | 63 |
| Ubiquinone + Diethylhexyl syringylidene malonate - (0.2%:0.5%) | 100 | 74 | 71 | 71 |
| Ubiquinone + Diethylhexyl syringylidene malonate - (0.2%:1.0%) | 100 | 93 | 90 | 87 |

Formulation Used for the Study Described in Example 6

| INCI name | Trade Name/Supplier | % w/w | % w/w |
|---|---|---|---|
| Phase A-1 | | | |
| Water (demineralized) | | 63.75 | 63.70 |
| Disodium EDTA | | 0.05 | 0.05 |
| Glycerin | | 5.00 | 5.00 |
| Phase A-2 | | | |
| Xantham gum | Vanzan NF/Vanderbilt | 0.25 | 0.25 |
| Phase B | | | |
| C12–15 Alkyl Benzoate | Finsolv TN/Finetex | 5.00 | 5.00 |
| Capric Caprylic Triglycerides | Myritol 318/Cognis | 5.00 | 5.00 |
| Diethylhexyl syringylidene malonate | Oxynex ST/Rona | 0.50 | |
| Ubiquinone | | 0.05 | 0.05 |
| Shea Butter | Cetiol SB-45/Cognis | 4.00 | 4:00 |
| Dimethicone | Dow corning 200, 100 cst/Dow Corning | 0.50 | 0.50 |
| Glyceryl Stearate, PEG-100 Stearate | Arlacel 165/Uniqema | 2.50 | 2.50 |
| Glyceryl Stearate | Cerasynt SD/ISP | 0.50 | 0.50 |
| Sorbitan Stearate | Arlacel 60/Uniquema | 1.00 | 1.00 |
| Stearic Acid | Emersol 132/Cognis | 1.50 | 1.50 |
| Phase C | | | |
| Triethanolamine 99% | | 0.06 | 0.06 |

| INCI name | Trade Name/Supplier | % w/w | % w/w |
|---|---|---|---|
| Phase D | | | |
| Phenoxyethanol, Isopropylparaben, Isobutylparaben, Butylparaben | Liquapar PE/Sutton | 1.00 | 1.00 |
| Total | | 100.00 | 100.00 |
| | | pH-6.8 | pH-6.9 |

Procedure: Combine A-1; disperse A2 in A1, which results in A, while stirring and heat A to 70° C. Combine ingredients of phase B then heat to 70° C. Add phase B to A with good mixing. Homogenize mixture at moderate speed, while cooling to 40° C. When temperature reaches 40° C. add premixed phase D; stir gently until mixture is homogeneous. Adjust pH with phase C to 4.8–5.5.

Example 7

Photostability of β Carotene Under Sun Simulator in Lotion, With and Without Diethylhexyl Syringylidene Malonate

| Sample description | Relative absorption of β carotene at 465 nm (%) | | | | |
|---|---|---|---|---|---|
| | 0 MED | 1 MED | 2 MED | 4 MED | 5 MED |
| β carotene (0.02%) | 100 | 65 | 27 | 2 | 0 |
| β carotene + Diethylhexyl syringylidene malonate - (0.02%:0.2%) | 100 | 84 | 65 | 38 | 35 |

Result: The concentration of β carotene is 0.02% while Diethylhexyl syringylidene malonate is present at 0.2%. Inclusion of Diethylhexyl syringylidene malonate (0.2%) in the lotion shows a clear improvement in the photostability of β carotene under sun simulator.

Example 7A

Photostability of β Carotene Under Room Temperature in Lotion, With and Without Diethylhexyl Syringylidene Malonate Result: Same study as described in the Example 7 was repeated except it was kept at room temperature and exposed to visible light for one month. Comparison of lotion with and without Diethylhexyl syringylidene malonate clearly showed that the lotion with Diethylhexyl syringylidene malonate has no discoloration over time. The lotion without Diethylhexyl syringylidene malonate clearly showed discoloration of the lotion, especially on the upper surface of the lotion.

Formulation Used for the Studies Described in Example 7 and 7A

| INCI name | Trade Name/Supplier | % w/w | % w/w |
|---|---|---|---|
| Phase A-1 | | | |
| Water (demineralized) | | 63.75 | 63.70 |
| Disodium EDTA | | 0.05 | 0.05 |
| Glycerin | | 5.00 | 5.00 |
| Phase A-2 | | | |
| Xantham gum | Vanzan NF/Vanderbilt | 0.20 | 0.20 |
| Phase B | | | |
| C12–15 Alkyl Benzoate | Finsolv TN/Finetex | 5.00 | 5.00 |
| Capric Caprylic Triglycerides | Myritol 318/Cognis | 5.00 | 5.00 |
| Beta-Carotene, Corn Oil | Beta-Carotene 15M/BASF | 0.14 | 0.14 |
| Diethylhexyl syringylidene malonate | Oxynex ST/Rona | 0.20 | |
| Shea Butter | Cetiol SB-45/Cognis | 3.5 | 3.5 |
| Dimethicone | Dow Corning 200, 100 cst/Dow Corning | 0.50 | 0.50 |
| Glyceryl Stearate, PEG-100 Stearate | Arlacel 165/Uniqema | 2.50 | 2.50 |
| Glyceryl Stearate | Cerasynt SD/ISP | 0.75 | 0.75 |
| Sorbitan Stearate | Arlacel 60/Uniquema | 0.75 | 0.75 |
| Stearic Acid | Emersol 132/Cognis | 1.50 | 1.50 |
| Phase C | | | |
| Triethanolamine | | 0.10 | 0.10 |
| Phase D | | | |
| Phenoxyethanol, Isopropylparaben, Isobutylparaben, Butylparaben | Liquapar PE/Sutton | 1.00 | 1.00 |
| Total | | 100.00 | 100.00 |

Procedure: Combine A-1; disperse A2 in A1, which results in A, while stirring and heat A to 70° C. Combine ingredients of phase B then heat to 70° C. Add phase B to A with good mixing. Homogenize mixture at moderate speed, while cooling to 40° C. When temperature reaches 40° add phase D; stir gently until mixture is homogeneous. Adjust pH with phase C to 4.8–5.5.

Notes pH value: 4.8; Viscosity: 24,000 cps (Brookfield RVT, spindle C, Helipath) at 25° C.

Example 8

Effect on Viscosity With and Without a Stabilizer

Lotion with 0.02% Beta-Carotene+0.2% Oxynex ST

| Formulation # EUS 24–63 INCI name | Trade Name/Supplier | Invention % w/w | Control % w/w |
|---|---|---|---|
| Phase A-1 | | | |
| Water (demineralized) | | 63.75 | 63.75 |
| Disodium EDTA | | 0.05 | 0.05 |
| Glycerin | | 5.00 | 5.00 |
| Phase A-2 | | | |
| Xantham gum | Vanzan NF/Vanderbilt | 0.20 | 0.20 |
| Phase B | | | |
| C12–15 Akyl Benzoate | Finsolv TN/Finetex | 5.00 | 5.00 |
| Capric Caprylic Triglycerides | Myritol 318/Cognis | 5.00 | 5.00 |
| Beta-Carotene, Corn Oil | Beta-Carotene 15M/BASF | 0.14 | 0.14 |
| Diethylhexyl syringal malonate | Oxynex ST/Rona | 0.20 | |
| Shea Butter | Cetiol SB-45/Cognis | 3.50 | 3.50 |
| Dimethicone | Dow Corning 200, 100 cst/Dow Corning | 0.50 | 0.50 |
| Glyceryl Stearate, PEG-100 Stearate | Arlacel 165/Uniqema | 2.50 | 2.50 |
| Glyceryl Stearate | Cerasynt SD/ISP | 0.75 | 0.75 |
| Sorbitan Stearate | Arlacel 60/Uniquema | 0.75 | 0.75 |
| Stearic Acid | Emersol 132/Cognis | 1.50 | 1.50 |
| Phase D | | | |
| Triethanolamine | | 0.10 | 0.10 |
| Phase E | | | |
| Phenoxyethanol, Isopropylparaben, Isobutylparaben, Butylparaben | Liquapar PE/Sutton | 1.00 | 1.00 |
| Total | | 100.00 | 100.00 |

Procedure: Combine A-1; disperse A2 in A1, which results in A, while stirring and heat A to 70° C. Combine ingredients of phase B then heat to 70° C. Add phase B to A with good mixing. Homogenize mixture at moderate speed, while cooling to 50° C. When temperature reaches 40° add phase D; stir gently until mixture is homogeneous. Adjust pH with phase C to 5.5–6.0

Notes pH value: 5.5; Viscosity: 24,000 cps (Brookfield RVT, spindle C, Helipath) at 25° C.

Lab Investigation Results:

| Formulation | Description | Observation @ 40° C. |
|---|---|---|
| Invention | Present invention | No significant changes |
| Control | No stabilizer (No Oxynex St) | Significant color change & viscosity dropping |
| Result: pH value: 4.8 | Vicosity (Control) | Initial: 24,000 cps After 1 month 18,000 cps; both measurements made @ 40° C. |
| | Viscosity (Invention) | Initial: 24,500 cps After 1 month 24,000 cps; both measurements made @ 40° C. |

The data clearly shows that the viscosity drop is minimal when the lotion contains a stabilizer of this invention.

Example 9

Shampoo Formulation with FD&C Greeen Color and a Stabilizer

| INCI name | Trade Name/ Supplier | % w/w | % w/w |
|---|---|---|---|
| Phase A | | | |
| Water deionized | | 85.90/ 86.00 | 343.60/ 344.00 |
| Water, Sodium Laureth Sulfate, Ethoxylated Fatty Alcohol, Sodium Chloride, Sodium Sulfate | Standapol ES-2/ Cognis | 10.00 | 40.00 |
| Water, Sodium Chloride, Sodium Glycolate, Cocamido Propylamine, Cocamido Propyl Betaine | Velvetex BK-35/ Cognis | 3.00 | 12.00 |
| | FD&C Green No. 3 (0.1% Soln.) | 1.00 | 4.00 |
| Phase B | | | |
| Diethylhexyl syringylidene malonate | Oxynex ST/Rona | 0.10/ 0.00 | 0.40/ 0.00 |
| Total | | 100.00 | 400.00 |

Procedure: Combine Phase A. Mix until mixture is homogeneous. Add phase B.

Result: Shampoo without a stabilizer shows significant loss of green color vs the shampoo with a stabilizer.

Example 10

Photostabilization Results of Natural Tocopherols in Ethanolic Solution

| | Relative absorption of Tocopherols at 298 nm (%) | | | |
|---|---|---|---|---|
| Sample Description | 0 MED | 2 MED | 5 MED | 10 MED |
| Tocopherols (0.02%) | 100 | 47 | 10 | 5 |
| Tocopherols + Diethylhexyl syringylidene malonate (0.02%:0.05%) | 100 | 87 | 82 | 77 |

Result—Inclusion of Diethylhexyl syringylidene malonate (0.05%) in the solution shows a clear improvement in the photostability of Tocopherols under sun simulator.

Example 11

Prophetic Formulations of Typical Exemplary Cosmetic, Personal Care & Household Formulations where Stabilizer(s) of the Present Invention can be Included The purpose of this inclusion is stabilization of formulation ingredients like, for example, antioxidant, color, photosensitive compounds, viscosity.

Formulation 1. Shower Gel
Stabilization of D&C Color Red #33

| | |
|---|---|
| Water | qs to 100 |
| Cocoamidopropyl betaine | 5.00 |
| Sodium laureth sulfate | 5.50 |
| Sodium lauryl sarcosinate | 0.50 |
| Polyquaternium-10 | 0.10 |
| Sodium sulfate | 2.10 |
| Polysorbate 2 | 1.00 |
| PEG-40 hydrogenated castor oil | 0.50 |
| Diethylhexyl syringylidene malonate | 0.50 |
| D&C Red #33 | 0.05 |
| DMDM Hydantoin | 0.60 |

Formulation 2. Moisturizing Cleansing Gel
Stabilization of FD&C Blue #1

| | |
|---|---|
| Water | qs to 100 |
| Sodium laureth sulfate | 16.00 |
| Lanolin alcohol | 2.50 |
| Cocamidopropyl betaine | 2.00 |
| Stearic acid | 1.25 |
| Glycereth-12 | 1.00 |
| Polyquaternium-10 | 0.25 |
| Glycerin | 5.00 |
| Diethylhexyl syringylidene malonate or Bis-diethylhexyl-3,5-dimethoxy-4-hydroxy-N-methyl malonamide or Bis-diisoamyl-3-methoxy-4-hydroxy-N-ethyl malonamide | 0.50 |
| FD&C Blue #1 | 0.01 |
| Phenoxyethanol | 0.60 |
| Methylparaben | 0.20 |
| Propylparaben | 0.10 |

Formulation 3. Skin Cleansing Bar Soap
Stabilization of Color and fragrance

| | |
|---|---|
| Sodium stearate | 24.00 |
| TEA lauryl sulfate | 18.00 |
| Acetamide MEA | 5.00 |
| Peg-45 palm kernel glycerides | 10.00 |
| Cocamide DEA | 20.00 |
| Propylene Glycol | 10.00 |
| Gycerin | 1.00 |
| Urea | 2.00 |
| Isoamyl-alpha-acetyl-3,5-dimethoxy 4-hydroxy cinnamate | 0.50 |
| 2-methyl-2-pentenoic acid | 0.10 |
| D&C Green #3 | 0.02 |

Formulation 4. Pearlescent Conditioning Shampoo
Stabilization of color and viscosity

| | |
|---|---|
| Water | qs to 100 |
| Guar hydroxyproyltrimonium Chloride | 0.5 |
| Hydroxypropyl methylcellulose | 0.60 |
| TEA-lauryl sulfate | 7.00 |
| Glycol stearate | 1.20 |
| Sodium lauroamphoacetate | 5.00 |
| Sodium trideceth sulfate | 3.00 |
| Cocamide DEA | 2.50 |
| Diethylhexyl syringylidene malonate or Bis-diethylhexyl-3,5-dimethoxy-4-hydroxy-N-methyl malonamide or Bis-diisoamyl-3-methoxy-4-hydroxy-N-ethyl malonamide | 0.50 |
| D&C Red #33 | 0.04 |
| FD&C Blue #1 | 0.01 |
| DMDM Hydantoin | 0.60 |

Formulation 5. Baby Shampoo
Stabilization of viscosity

| | |
|---|---|
| Water | qs to 100 |
| PEG-80 sorbitan laurate | 12.00 |
| Sodium trideceth sulfate | 5.00 |
| Sodium lauroamphoacetate | 5.00 |
| PEG-120 methyl glucose dioleate | 2.00 |
| Cocamidopropyl hydroxysultaine | 1.00 |
| Polysorbate 20 | 0.80 |
| Diethylhexyl syringylidene malonate | 0.10 |
| Guaiazulene | 0.010 |

-continued

| | |
|---|---|
| DMDM Hydantoin | 0.50 |

Formulation 6. Rinse off Conditioner
Stabilization of color and fragrance

| | |
|---|---|
| Water | qs to 100 |
| Glycerin | 2.00 |
| Disodium EDTA | 0.10 |
| Steramidopropyl dimethylamine lactate | 2.00 |
| Cetyl alcohol | 2.50 |
| Stearyl alcohol | 2.00 |
| Dimethicone | 2.50 |
| Cyclomethicone | 3.00 |
| Lactic acid | 0.50 |
| Diethylhexyl syringylidene malonate | 1.00 |
| 3-cyclohexene-1-carboxaldehyde, 2,4-dimethyl | 0.40 |
| D&C Green #3 | 0.01 |

Formulation 7. Aerosol Hair Spray (Hydroalcoholic, moderate VOC)
Stabilization of colors

| | |
|---|---|
| SD alcohol 40B | 40.00 |
| PVP K-30 | 3.00 |
| Lauramide DEA | 0.50 |
| Dimethicone copolyol | 0.50 |
| Phenyl trimethicone | 0.10 |
| Ethyl-alpha-acetyl-3-methoxy-4-hydroxy cinnamate or Bis-diethylhexyl-3,5-dimethoxy-4-hydroxy-N-methyl malonamide or Bis-diisoamyl-3-methoxy-4-hydroxy-N-ethyl malonamide | 0.50 |
| FD&C Red #33 | 0.10 |
| FD&C Blue #1 | 0.01 |
| Water | 25.00 |
| Dimethyl ether | 21.00 |
| Propane and butane (LPG propellant A-46) | 9.00 |

Formulation 8. Hair styling gel
Stabilization of polymer and viscosity

| | |
|---|---|
| Water | qs |
| Carbomer | 0.50 |
| Glycerin | 1.00 |
| Panthenol | 0.10 |
| Disodium EDTA | 0.05 |
| PVP K-30 | 2.00 |
| Diethylhexyl syringylidene malonate or Bis-N-[3-(N,N-dimethylmethylammonium)propyl]3,5-dimethoxy 4-hydroxy benzylidene malonamide bis chloride | 0.50 |
| Polysorbate-20 | 1.00 |
| Peg-40 Hydrogenated Castor oil | 0.50 |
| FD&C Blue #1 | 0.01 |
| Aminomethylpropanol | 0.50 |
| Diazolidinyl urea | 0.30 |

Formulation 9. Styling Mousse
Stabilization of color

| | |
|---|---|
| Water | qs |
| Polyquaternium-11 | 2.00 |
| Oleth-20 | 2.00 |
| Peg-40 hydrogenated Castor oil | 1.00 |
| 2-Ethylhexyl-alpha-acetyl-3,5-diemthoxy-4-hydroxy cinnamte or Bis-N-[3-(N,N-dimethyllaurylammonium)propyl]3,5-dimethoxy 4-hydroxy benzylidene malonamide bis tosylate | 0.50 |
| FD&C Red #40 | 0.01 |
| FD&C Yellow #5 | 0.01 |
| DMDM Hydantoin | 0.60 |
| Isobutane(80%) and Propane(20%) | 10.00 |

Formulation 10. Temporary Hair color
Stabilization of color & viscosity

| | |
|---|---|
| Propylene Glycol | 3.00 |
| Hydroxyethylcellulose | 1.00 |
| Sodium hydroxide | 0.04 |
| Methyl paraben | 0.20 |
| DMDM hydantoin | 0.50 |
| Diethylhexyl syringylidene malonate or Bis-N-[3-(N,N-dimethylmethylammonium)propyl]3,5-dimethoxy 4-hydroxy benzylidene N-methyl malonamide bis chloride or Bis-N-[3-(N,N-dimethylmethylammonium)propyl]3-methoxy 4-hydroxy benzylidene malonamide bis methosulfate | 0.50 |
| Polysorbate 20 | 1.00 |
| FD&C Blue #1 | 0.04 |
| D&C Orange #4 | 0.20 |
| D&C Yellow #10 | 0.03 |
| D&C Green #5 | 0.02 |
| FD&C Red #4 | 0.05 |
| Water | qs |

Formulation 11. O/W lotion
Stabilization of color

| | |
|---|---|
| Water | qs |
| Glycerin | 5.00 |
| Disodium ETDA | 0.10 |
| Xantham Gum | 0.20 |
| Isopropyl Palmitate | 5.00 |
| Caprylic/Capric triglycerides | 3.00 |
| Apricot Kernel oil | 3.00 |
| Glyceryl stearate | 2.50 |
| Peg-100 stearate | 1.50 |
| Dimethicone | 1.00 |
| Stearic acid | 1.50 |
| Triethanolamine | 0.10 |
| Phenoxyethanol | 0.60 |
| Methylparaben | 0.20 |
| Propylparaben | 0.10 |
| Diethylhexyl syringylidene malonate | 0.10 |
| D&C Green #3 | 0.01 |
| Fragrance | 0.10 |

Formulation 12. Self tanner foam
Stabilization of color

| | |
|---|---|
| Water | qs |
| Cetyl hydroxyethylcellulose | 0.25 |
| Sorbitol | 2.50 |
| Propylene Glycol | 5.00 |
| Dihydroxyacetone | 6.00 |
| Decyl Glucoside | 1.50 |
| Polysorbate 20 | 1.00 |
| Diethylhexyl syringylidene malonate | 0.50 |
| Carmine | 0.30 |
| FD&C Yellow #5 | 0.05 |
| FD&C Blue #1 | 0.02 |
| Caramel | 0.50 |
| Citric Acid | 0.04 |
| Phenoxyethanol | 0.50 |
| Methylparaben | 0.20 |
| Propylparaben | 0.10 |
| Fragrance | 0.10 |

Formulation 13. Skin Toner
Stabilization of color

| | |
|---|---|
| Water | qs |
| SD alcohol 40B | 15.00 |
| Glycerin | 5.00 |
| Aloe vera gel | 3.00 |
| Polysorbate 20 | 1.00 |
| Peg-40 hydrogenated castor oil | 0.50 |
| Diethylhexyl syringylidene malonate | 0.20 |
| FD&C blue #1 | 0.01 |
| D&C Red #33 | 0.01 |
| Methylparaben | 0.20 |
| DMDM hydantoin | 0.50 |
| Fragrance | 0.10 |

Formulation 14. Facial Cleanser
Stabilization of color and viscosity

| | |
|---|---|
| Water | 60.00 |
| Propylene glycol | 1.00 |
| Peg-150 pentaerythrityl tetrastearate | 1.50 |
| Dimethicone copolyol | 5.00 |
| Disodium cocoamphoacetate | 3.50 |
| Sodium lauroyl sarcosinate | 3.50 |
| Citric acid | qs to pH-6 |
| Diethylhexyl syringylidene malonate | 0.20 |
| Chlorophyll copper | 0.01 |

| | |
|---|---|
| DMDm Hydantoin | 0.60 |

Formulation 15. Clear deodorant
Stabilization of fragrance

| | |
|---|---|
| Water | 5.00 |
| Propylene glycol | 46.75 |
| Sodium Stearate | 8.00 |
| PPG-3 myristyl ether | 39.00 |
| Triclosan | 0.25 |
| Diethylhexyl syringylidene malonate | 2.00 |
| FD&C Blue #1 | 0.01 |
| 3-cyclohexene-1-carboxaldehyde,1-methyl-4-(4-methyl-3-pentenyl) | 0.5% |

Formulation 16. Clear Gel Toothpaste
Stabilization of color & maintenance of product integrity

| | |
|---|---|
| Water | qs to 100 |
| Glycerin | 10.00 |
| Sorbitol(70%) | 30.00 |
| PEG-32 | 5.00 |
| Hydrated silica abrasive | 15.00 |
| Hydrated silica thickener | 8.00 |
| Sodium sachharin | 0.30 |
| Sodium monofluoro phosphate | 0.80 |
| Sodium lauryl sulfate | 1.30 |
| Diethylhexyl syringylidene malonate | 0.50 |
| Polysorbate 20 | 1.00 |
| FD&C Blue #1 | 0.05 |
| Flavor | 1.00 |

Formulation 17. Hydroalcoholic Mouthwash
Stabilization of color

| | |
|---|---|
| Water | 75.18 |
| Glycerin | 8.00 |
| Sodium benzoate | 0.10 |
| Benzoic acid | 0.04 |
| Sodium saccharin | 0.08 |
| Cetylpyridinium chloride | 0.05 |
| FD&C Blue #1 | 0.02 |
| SDA alcohol 40B | 15.00 |
| Polysorbate20 | 1.00 |
| Diethylhexyl syringylidene malonate or Bis-N-[N,N-dimethylethylammonium)propyl]3,5-dimethoxy 4-hydroxy benzylidene malonamide bis chloride | 0.50 |

Formulation 18. Insect Repellent lotion
Stabilization of color and insect repellant

| | |
|---|---|
| Water | qs to 100 |
| Glycerin | 5.00 |
| Disodium EDTA | 0.10 |
| Xanthan Gum | 0.25 |
| Ethyl Butylaminopropionate | 10.00 |
| PPG-3 Benzyl Ether Myristate | 2.50 |
| Isopropyl myristate | 3.00 |
| Glyceryl stearate | 2.00 |
| PEG-100 stearate | 1.00 |
| Stearic acid | 1.00 |
| Cetyl alcohol | 1.50 |
| Phenoxyethanol | 0.60 |
| Methylparaben | 0.20 |
| Propylparaben | 0.10 |
| Diethylhexyl syringylidene malonate | 0.50 |
| FD&C Blue #1 | 0.05 |
| Fragrance | 0.10 |

Formulation 19. Lipstick
Stabilization of color

| | |
|---|---|
| Castor oil | 7.70 |
| Candelilla wax | 2.30 |
| Carnauba wax | 2.00 |
| Ozokerite | 2.00 |
| Microcrystalline wax | 4.00 |
| Caprylic/capric triglycerides | 25.00 |
| Octyldodecanol | 6.00 |
| Methylparaben | 0.20 |
| Propylparaben | 0.10 |
| Diethylhexyl syringylidene malonate | 1.00 |
| D&C Red #27 | 0.10 |
| FD&C Red #21 | 0.20 |
| FD&C Yellow #5 Aluminum Lake | 0.10 |

Formulation 20. Lipgloss
Maintenance of product integrity

| | |
|---|---|
| Polyisobutene | 30.00 |
| Petrolatum | 25.00 |
| Ozokerite | 5.00 |
| Microcrystalline wax | 1.00 |
| Octyldodecanol | 10.00 |
| Castor oil | qs to 100 |
| Diethylhexyl syringylidene malonate | 0.50 |
| D&C Red #22 aluminum lake | 0.05 |
| Titanium dioxide | 0.10 |
| Methylparaben | 0.20 |
| Propylparaben | 0.10 |

Formulation 21. Nail Lacquer
Stabilization of color

| | |
|---|---|
| Butyl acetate | 42.00 |
| Ethyl acetate | 18.10 |
| Stearalkonium hectorite | 1.20 |
| Dibutyl phthalate | 5.00 |
| Tosylamide/formaldehyde resin | 7.00 |
| Isopropanol | 8.00 |
| Nitrocellulose | 4.00 |
| Diethylhexyl syringylidene malonate or Bis-N-[3-(N,N-dimethylmethylammonium)propyl]3,5-dimethoxy 4-hydroxy benzylidene malonamide bis chloride | 0.40 |
| D&C Red #27 Aluminum lake | 0.10 |
| D&C Red #34 Calcium lake | 0.10 |

Formulation 22. Dishwashing Liquid
Stabilization of color and maintenance of product integrity

| | |
|---|---|
| Water | 42.00 |
| Carbomer | 1.00 |
| Ammonium lauryl sulfate | 7.00 |
| Sodium laureth sulfate | 7.50 |
| Diethylhexyl syringylidene malonate | 0.50 |
| Polysorbate 20 | 1.00 |
| D&C Red #33 | 0.01 |
| FD&C Blue #1 | 0.01 |
| Sodium citrate | 0.50 |
| Sodium hydroxide | 0.90 |

Formulation 23. Liquid Laundry Detergent
Stabilization of color & fragrance

| | |
|---|---|
| Water | qs to 100 |
| Sodium lauryl sulfate | 7.50 |
| Stearic Acid | 3.00 |
| Palmitic Acid | 3.50 |
| C14–15 Pareth-7 | 17.00 |
| Triethanolamine | 7.50 |
| Propylene glycol | 12.00 |
| Citric acid | 3.25 |
| Potassium hydroxide | 4.25 |
| Diethylhexyl syringylidene malonate | 4.00 |
| FD&C Blue #1 | 0.01 |
| 2-ethyl hexanal cycloglycol acetate | 1.00 |

Example 12

Color Stabilizing Effect of Cationic Antioxidant-Sunscreens of the Present Invention Structure of the Stabilizer Used (Present Invention):
Bis-N-[3'-(N',N'-Dimethylethylammonium)propyl]-3,5-dimethoxy-4-hydroxy benzylidene malonamide bis ethyl sulfate Parameters Used for the Study:

| Color Stability Protocol | Time Range | Type of evaluation |
|---|---|---|
| Shampoo formulation with 0.1% stabilizer and 0.01% Dye | 1. 10 days UV-A irradiation (8 hrs/day) 5 days UV-B irradiation (8 hrs/day) | Visual |

Lab Investigation Results

| Formulation | Description | UV-A | UV-B |
|---|---|---|---|
|  | Green # 3 |  |  |
| A | No Stabilizer | + | + |
| B | Present Invention | +++ | ++ |
|  | Blue # 1 |  |  |
| A | No stabilizer | + | + |
| B | Present Invention | +++ | ++ |
|  | Red # 40 |  |  |
| A | No Stabilizer | + | + |
| B | Present Invention | ++ | ++ |

+ Extreme color fading
++ Some color fading
+++ No color fading

Shampoo Formulation Used in the Stability Study:

| INCI Name | Trade Name/Supplier | % w/w |
|---|---|---|
| Water deionized |  | 86.00 (for A) or 85.9 (for B) |
| Water, Sodium Laureth Sulfate, Ethoxylated Fatty Alcohol, Sodium Glycolate, Sodium Chloride, Sodium Sulfate | Standapol ES-2/Cognis | 10.00 |
| Water, Sodium Chloride, Sodium Glycolate, Cocamido Propylamine, Cocamido Propyl Betaine | Velvetex BK-35/Cognis | 3.00 |
|  | FD&C Color/ Green # 3 or Blue # 1 or Red # 40 (0.1% soln) | 1.00 |
| Stabilizer | Present Invention | 0 (for A) or 0.1% (for B) |

Example 13

Comparative Singlet Oxygen Quenching Ability of Vitamin E, Ascorbic Acid, Oxynex ST, Eusolex ASA and HP A solution of N,N-dimethyl-p-nitrosoaniline (RNO) and histidine and a known sensitizer (e.g. methylene blue) is exposed to UV A. Singlet oxygens generated under UV A induce a bleaching of RNO which can be measured spectrophotometrically at 440 nm. The efficiency of test products in terms of singlet oxygen scavenging is measured at 440 nm for various concentrations.

All measurements were performed at room temperature (24 C) with a Beckman Coulter DU-640 spectrophotometer at a scan speed of 120 nm/min with a spectral range from 300 to 700 nm.

a) Stock Solutions:
Buffer Solution
    $KH_2PO_4$ 99.8% & KOH 85+% (pH 7.4, 50 mM)
    Mol. Wt. 136.09, VWR and Sigma-Aldrich
    $KH_2PO_4$ (681 mg) dissolved in distilled water (100 ml) and pH adjusted to 7.0–7.1 with a 2 M KOH solution
N,N-dimethyl-p-nitrosoaniline (RNO) Solution (50 µM)
    Mol. Wt. 150, Sigma-Aldrich
    RNO (19 mg) dissolved in 50 ml of Buffer solution subsequent dilution by factor 25 in de-ionized water.
L-Histidine Solution (40 mM)
    Mol. Wt. 155, Sigma-Aldrich
    62 mg are dissolved in distilled water (10 ml)
Methylene Blue Solution (50 µM)
    Mol. Wt. 320, Sigma-Aldrich
    5 mg are dissolved in distilled water (100 ml) subsequent dilution at 6.4 ml in 25 ml of de-ionized water.

b) Antioxidant Solutions:
Ascorbic acid (0.5 mM)
    Mol. Wt. 176.1, Sigma-Aldrich
    Kojic acid (8.8 mg) dissolved in distilled water (100 ml)
Trolox C, 98% (15 mM) (*)
    (S-hydroxy-tetramethylchroman carboxylic acid)
    Mol. Wt. 250.29, Sigma-Aldrich
    Trolox C (37.5 mg) dissolved in ethanol:distilled water (1:1, 10 ml)
Oxynex ST™, 99.5% (2.7 mM) (*)
    (Di-2-ethylhexyl 3,5 dimethoxy 4 hydroxy benzylidene malonate)
    Mol. Wt. 492, EMD Chemicals
    Oxynex ST™ (20 mg) dissolved in ethanol:distilled water (2:1, 15 ml)
Eusolex ASA™, purity higher than 97% (*)
    (Isoamyl alpha acetyl-3,5 dimethoxy 4 hydroxy benzylidene malonate)
    Mol. Wt. 335, EMD Chemicals
    Eusolex ASA™ (18 mg) dissolved in ethanol:distilled water (2:1, 15 ml)
Eusolex HP™, purity higher than 97%
    (Bis-N[3'-(N,N dimethylamino)propyl]-3,5-dimethoxy-4 hydroxybenzylidene malonamide bis ethyl sulfate)
    Mol. Wt. 694, EMD Chemicals
    Eusolex HP™ (21 mg) dissolved in distilled water (10 ml)
    (*) Results have to be corrected by the respective alcoholic:aqueous solutions because methanol and ethanol increase singlet oxygen generation but only slightly. The RNO tests were therefore repeated for the corresponding liquid phases (1:1 v/v of ethanol and water, or pure ethanol) without additional antioxidant.

IMPORTANT: The test has to be performed under experimental conditions so that secondary products cannot accumulate and that RNO bleaching does not exceed 15% of its initial concentration. Therefore, all present concentrations are adjusted as to give a RNO absorption band (440 nm) relative decrease of less than 15% when combined with 20 min UV A exposure time.

Procedure:

The stock solutions were added in an orderly manner with quantities according to the table below as to obtain a final total volume of 4.5 ml for each preparation. First, the RNO buffered solution was taken, followed by addition of L-Histidine and the sensitizer Methylene Blue. Then, the antioxidant solution was added and topped off to 4.5 ml total volume with buffer solution. This preparation was exposed to UV A radiation (~35 W/m$^2$) for 20 min to generate singlet oxygens. The light absorption spectra were then recorded and the optical density measured at 440 nm (corresponding to RNO). The inverse of the light absorbances at 440 nm is then plotted as a function of the concentration in antioxidant.

| Preparation | RNO solution | L-Histidine solution | Methylene Blue solution | Antioxidant stock solution | Buffer stock solution |
|---|---|---|---|---|---|
| A | 2.0 ml | 1.0 ml | 1.0 ml | — | 0.5 ml |
| B | 2.0 ml | 1.0 ml | 1.0 ml | 0.1 ml | 0.4 ml |
| C | 2.0 ml | 1.0 ml | 1.0 ml | 0.2 ml | 0.3 ml |
| D | 2.0 ml | 1.0 ml | 1.0 ml | 0.4 ml | 0.1 ml |
| E | 2.0 ml | 1.0 ml | 1.0 ml | 0.5 ml | — |

Results and Discussion:

Results shown in FIG. 3 and the table below demonstrate that Oxynex ST (Diethylhexy syringylidene malonate) and Eusolex ASA (isoamyl-alpha-acetyl-3,5-dimethoxy-4-hydroxy cinnamte) and Eusolex HP (Bis-N-[3'-(N',N'-Dimethylethylammonium)propyl]-3,5-dimethoxy-4-hydroxy benzylidene malonamide bis ethyl sulfate) behave as an efficient singlet oxygen scavengers, better than Vitamin E, the activity of which was inferred from Trolox C after correction on a weight basis. Ascorbic acid behaves as a pro-oxidant. IC$_{50}$% concentration values are given in the table below. Eusolex ASA exhibits the best efficiency as an antioxidant, followed by Oxynex ST and Eusolex HP.

IC$_{50}$% concentrations of singlet oxygen quenching ability of products of the present invention and other antioxidants are given below:

| Antioxidant | IC$_{50\%}$ (µg/ml) |
|---|---|
| Trolox C | 88 |
| Ascorbic acid | Pro-oxidant |
| Eusolex HP ™ | 104 |
| Oxynex ST ™ | 80 |
| Eusolex ASA ™ | 61 |

The preceding examples can be repeated with similar success by substituting the generically or specifically described reactants and/or operating conditions of this invention for those used in the examples.

From the foregoing description, one skilled in the art can easily ascertain the essential characteristics of this invention, and without departing from the spirit and scope thereof, can make various changes and modifications of the invention to adapt it to various usages and conditions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosure of all applications, patents and publications, cited herein and of corresponding U.S. Provisional Application No. 60/565,843, filed Apr. 28, 2004 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of stabilizing at least one photosensitive poly-unsaturated and/or aromatic compound which is either a color compound, antioxidant, a fragrance compound, a flavor compound or a combination thereof, said method comprising combining at least one compound of formulae ii, ii' and/or i" with said at least one photosensitive poly-unsaturated and/or aromatic compound in a ratio within a range of 10:1 to 1:2 based on total weight percent of the one or more compounds of formulae ii, ii' and/or i" to the total weight percent of the one or more photosensitive poly-unsaturated and/or aromatic compounds,

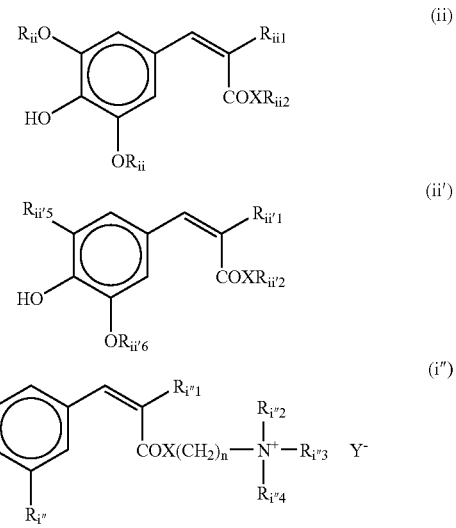

wherein each $R_{ii}$ is independently linear or branched $C_1$ to $C_8$ alkyl;

$R_{ii1}$ is —C(O)CH$_3$, —CO$_2$R$_{ii3}$, —C(O)NH$_2$, —C(O)N(R$_{ii4}$)$_2$, or —CN;

X is O, NH or N-alkyl;

$R_{ii2}$ is linear or branched $C_1$ to $C_{20}$ alkyl;

$R_{ii3}$ is linear or branched $C_1$ to $C_{20}$ alkyl;

each $R_{ii4}$ is independently hydrogen or linear or branched $C_1$ to $C_8$ alkyl;

$R_{ii'1}$ is —C(O)CH$_3$, —CO$_2$R$_{ii'3}$, —C(O)NH$_2$, —C(O)N(R$_{ii'4}$)$_2$, or —CN;

$R_{ii'2}$ is linear or branched $C_1$ to $C_{30}$ alkyl;

$R_{ii'3}$ is linear or branched $C_1$ to $C_{20}$ alkyl;

each $R_{ii'4}$ is independently hydrogen or linear or branched $C_1$ to $C_8$ alkyl;

$R_{ii'5}$ is linear or branched $C_1$–$C_8$ alkyl or hydrogen;

$R_{ii'6}$ is linear or branched $C_1$–$C_8$ alkyl;

each $R_{i''}$ is independently linear or branched $C_1$ to $C_8$ alkyl, or linear or branched $C_1$ to $C_8$ alkoxy; or one $R_{i''}$ is H and the other $R_{i''}$ is linear or branched $C_1$ to $C_8$ alkyl, or linear or branched $C_1$ to $C_8$ alkoxy, $R_{i''1}$ is COCH$_3$, CO$_2$R$_{i''5}$, CONH$_2$, CONH(R$_{i''6}$)$_2$, CN, COX(CH$_2$)n-N—(R$_{i''2}$)(R$_{i''4}$)(R$_{i''3}$), or the quaternized salt form of the formula COX(CH$_2$)n-N—(R$_{i''2}$)(R$_{i''4}$)(R$_{i''3}$)$^+$Y$^-$, n is an integer of 1 to 5, Y$^-$ is an anion, $R_{i''2}$, $R_{i''3}$ and $R_{i''4}$ are independently linear or branched $C_1$ to $C_{20}$ alkyl; and $R_{i''5}$ and $R_{i''6}$ are independently hydrogen or linear or branched $C_1$–$C_{20}$ alkyl.

2. A method according to claim 1, wherein the ratio of the one or more compound (s) of formulae ii, ii' and/or i" to the one or more photosensitive poly-unsaturated and/or aromatic compound(s) is 5:1 to 1:1.

3. A method according to claim 1, wherein only one photosensitive poly-unsaturated and/or aromatic compound is stabilized and the ratio of the one or more compound(s) of formulae ii, ii' and/or i" to the one photosensitive poly-unsaturated and/or aromatic compound is 10:1 to 1:1 and the one photosensitive poly-unsaturated and/or aromatic compound is a color compound, an antioxidant, a fragrance compound or a flavor compound.

4. A method according to claim 1, wherein the at least one compound of formulae ii, ii' and/or i" is at least one compound of formulae iii, iii', iv and/or iv'

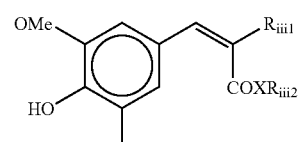

(iii)

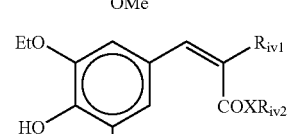

(iv)

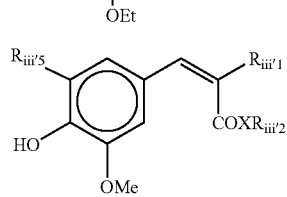

(iii')

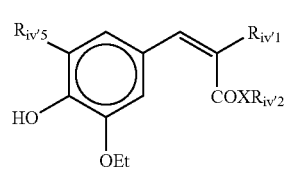

(iv')

wherein $R_{iii1}$ is —C(O)CH$_3$, —CO$_2$R$_{ii3}$, —C(O)NH$_2$, —C(O)N(R$_{ii4}$)$_2$, or —CN, $R_{iii2}$ is linear or branched $C_1$ to $C_{20}$ alkyl, $R_{iv1}$ is —C(O)CH$_3$, —CO$_2$R$_{ii3}$, —C(O)NH$_2$, —C(O)N(R$_{ii4}$)$_2$, or —CN, $R_{iv2}$ is linear or branched $C_1$ to $C_{20}$ alkyl, $R_{iii'1}$ is —C(O)CH$_3$, —CO$_2$R$_{ii'3}$, —C(O)NH$_2$, —C(O)N(R$_{ii'4}$)$_2$, or —CN, $R_{iii'2}$ is linear or branched $C_1$ to $C_{30}$ alkyl, $R_{iii'5}$ is linear or branched $C_1$–$C_8$ alkyl or hydrogen, $R_{iv'1}$ is —C(O)CH$_3$, —CO$_2$R$_{ii'3}$, —C(O)NH$_2$, —C(O)N(R$_{ii'4}$)$_2$, or —CN, $R_{iv'2}$ is linear or branched $C_1$ to $C_{30}$ alkyl, and $R_{iv'5}$ is linear or branched $C_1$–$C_8$ alkyl or hydrogen, wherein $R_{ii3}$, $R_{ii4}$, $R_{ii'3}$, and $R_{ii'4}$ are defined as in claim 1.

5. A method according to claim 1, wherein $R_{ii2}$, $R_{ii'2}$, $R_{ii3}$ and $R_{ii'3}$ are each a linear or branched $C_1$ to $C_8$ alkyl.

6. A method according to claim 1, wherein the compound of formulae ii, ii' and/or i" is ethyl-alpha-cyano-3,5-dimethoxy-4-hydroxy cinnamate, ethyl-alpha-acetyl-3,5-dimethoxy-4-hydroxy cinnamate, iso-propyl-alpha-acetyl-3,5-dimethoxy-4-hydroxy cinnamate, iso-amyl-alpha-acetyl-3,5-dimethoxy-4-hydroxy cinnamate, 2-ethylhexyl-alpha-acetyl-3,5-dimethoxy-4-hydroxy cinnamate, diethyl-3,5-dimethoxy-4-hydroxy benzylidene malonate, di-(2-ethylhexyl)-3,5-dimethoxy-4-hydroxy benzylidene malonate, diisoamyl-3,5-dimethoxy-4-hydroxy benzylidene malonate, didodecyl-3,5-dimethoxy-4-hydroxy benzylidene malonate, dipalmitoyl-3,5-dimethoxy-4-hydroxy benzylidene malonate, di-isopropyl-3,5-dimethoxy-4-hydroxy benzylidene malonate, ethyl-alpha-cyano-3-methoxy-4-hydroxy cinnamate, ethyl-alpha-acetyl-3-methoxy-4-hydroxy cinnamate, iso-propyl-alpha-acetyl-3-methoxy-4-hydroxy cinnamate, iso-amyl-alpha-acetyl-3-methoxy-4-hydroxy cinnamate, 2-ethylhexyl-alpha-acetyl-3-methoxy-4-hydroxy cinnamate, diethyl-3-methoxy-4-hydroxy benzylidene malonate, di-(2-ethylhexyl)-3-methoxy-4-hydroxy benzylidene malonate, diisoamyl-3-methoxy-4-hydroxy benzylidene malonate, didodecyl-3-methoxy-4-hydroxy benzylidene malonate, dipalmitoyl-3-methoxy-4-hydroxy benzylidene malonate, di-isopropyl-3-methoxy-4-hydroxy benzylidene malonate,

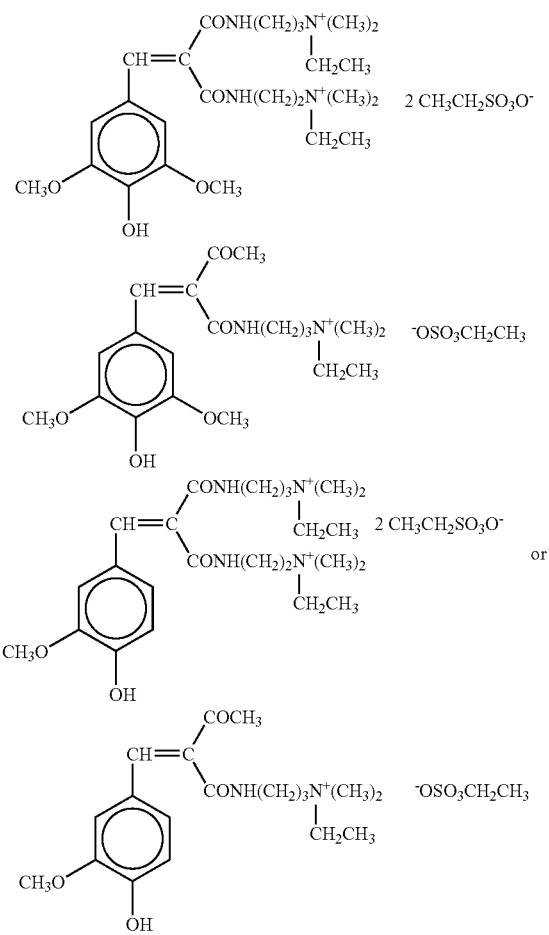

7. A method according to claim 1, wherein the compound of formulae ii, ii' and/or i" is
Di-2-ethylhexyl 3,5 dimethoxy 4 hydroxy benzylidene malonate,
Isoamyl alpha acetyl-3,5 dimethoxy 4 hydroxy benzylidene malonate, or
Bis-N[3'-(N,N dimethylamino)propyl]-3,5-dimethoxy-4 hydroxybenzylidene malonamide bis ethyl sulfate.

8. A method according to claim 1, wherein the one or more photosensitive compound(s) is protected from both visible light and UV.

9. A method according to claim 1, wherein the one or more photosensitive compound(s) is protected from visible light only or from substantially visible light only.

10. A method as in claim 1, wherein said one or more photosensitive poly-unsaturated and/or aromatic compound (s) is combined with at least one compound of formula ii, ii' and/or i" within a cosmetic composition, personal care product or household product, wherein the at least one compound of formula ii, ii' and/or i" is used in an amount of about 0.001 to 10.0 wt %, based on the total weight of the cosmetic composition, personal care product or household product.

11. A method as in claim 1, wherein said one or more photosensitive poly-unsaturated and/or aromatic compound(s) is combined with at least one compound of formula ii, ii' and/or i" within a cosmetic composition, personal care product or household product, wherein the at least one compound of formula ii, ii' and/or i" is used in an amount of about 0.01 to 4.0 wt %, based on the total weight of the cosmetic composition, personal care product or household product.

12. A method as in claim 1, wherein said one or more photosensitive poly-unsaturated and/or aromatic compound(s) is combined with at least one compound of formula ii, ii' and/or i" within a cosmetic composition, personal care product or household product, wherein the at least one compound of formula ii, ii' and/or i" is used in an amount of about 0.01 to 1.0 wt %, based on the total weight of the cosmetic composition, personal care product or household product.

13. A method as in claim 10, wherein the cosmetic composition, personal care product or household product is within a container for retail sale when the combination is formed.

14. A method as in claim 10, comprising the additional step of transferring the combination of at least one photosensitive poly-unsaturated and/or aromatic compound and at least one compound of formula ii, ii' and/or i" to a cosmetic composition, personal care product or household product within a container for retail sale, wherein the at least one compound of formula ii, ii' and/or i" is used in an amount of 0.001 to 10.0 wt %, based on the total weight of the cosmetic composition, personal care product or household product.

15. A method as in claim 10, comprising the additional step of transferring the combination of at least one photosensitive poly-unsaturated and/or aromatic compound and at least one compound of formula ii, ii' and/or i" to a cosmetic composition, personal care product or household product within a container for retail sale, wherein the at least one compound of formula ii, ii' and/or i" is used in an amount of 0.01 to 4.0 wt %, based on the total weight of the cosmetic composition, personal care product or household product.

16. A method according to claim 1, wherein the photosensitive compound is a carotenoid, tocopherol, guaiazulene, vanillin or menthylanthranillate.

17. A method as in claim 1, wherein the photosensitive poly-unsaturated color compound is a carotenoid, Ubiquinone or Azulene.

18. A method as in claim 17, wherein the Azulene photosensitive poly-unsaturated color compound is azulene, guaiazulene, or guaiol.

19. A method as in claim 17, wherein the carotenoid photosensitive poly-unsaturated color compound is Lycopene, Zeaxanthine, Cantaxanthine, α-, β- γ- & δ-Carotenes, Astacin, Astaxanthin, Chrysanthemaxanthin, Torularhodin, Violaxanthin, Capsanthin or Capsorubin.

20. A method as in claim 17, wherein the Ubiquinone photosensitive poly-unsaturated color compound is photosensitive Coenzyme $Q_n$ in which n=1–12.

21. A method as in claim 1, wherein the photosensitive poly-unsaturated color compound is a photosensitive dye or organic pigment.

22. A method as in claim 21, wherein the photosensitive organic pigment is a curcuminoid.

23. A method as in claim 21, wherein the curcuminoid is curcumin, Cassumunin A, Cassumunin B, demethoxycurcumin or bisdemethoxycurcumin.

24. A method according to claim 1, wherein said photosensitive poly-unsaturated compound is a fragrance that is combined with at least one compound of formula ii, ii' and/or i", wherein the at least one compound of formula ii, ii' and/or i" is used in an amount of about 0.001 to 10.0 wt %, based on the total weight of the resultant composition, and wherein the fragrance is 25. A method according to claim 1, wherein said photosensitive poly-unsaturated compound is a flavor that is combined with at least one compound of formula ii, ii' and/or i", wherein the at least one compound of formula ii, ii' and/or i" is used in an amount of 0.001–10 wt %, based on the total weight of the resultant composition, and wherein the flavor is

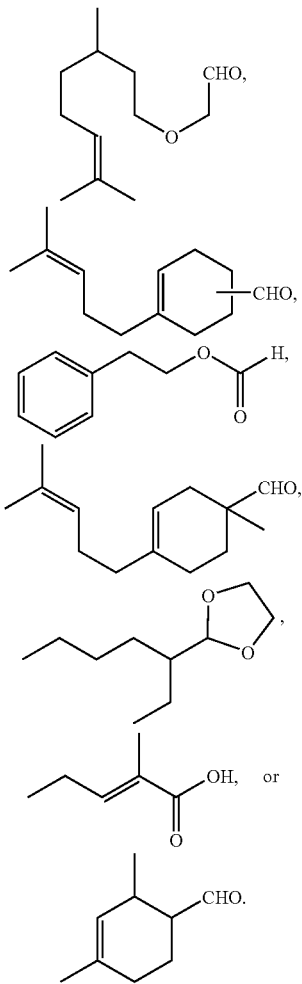

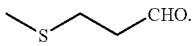

26. A product which is a cosmetic composition, personal care product or household product which contains at least one photosensitive poly-unsaturated and/or aromatic compound which is either a color compound, antioxidant, a fragrance compound, a flavor compound or a combination thereof,
wherein said photosensitive poly-unsaturated and/or aromatic compound is stabilized by the method of claim 1.

27. A product which is a cosmetic composition, personal care product or household product which contains at least one photosensitive poly-unsaturated and/or aromatic compound which is either a color compound, antioxidant, a fragrance compound, a flavor compound or a combination thereof,
wherein said photosensitive poly-unsaturated and/or aromatic compound is stabilized by the method of claim 5.

28. A product which is a cosmetic composition, personal care product or household product which contains at least one photosensitive poly-unsaturated and/or aromatic compound which is either a color compound, antioxidant, a fragrance compound, a flavor compound or a combination thereof,
wherein said photosensitive poly-unsaturated and/or aromatic compound is stabilized by the method of claim 10.

29. A product which is a cosmetic composition, personal care product or household product which contains at least one photosensitive poly-unsaturated and/or aromatic compound which is either a color compound, antioxidant, a fragrance compound, a flavor compound or a combination thereof,
wherein said photosensitive poly-unsaturated and/or aromatic compound is stabilized by the method of claim 11.

30. A product which is a cosmetic composition, personal care product or household product which contains at least one photosensitive poly-unsaturated and/or aromatic compound which is either a color compound, antioxidant, a fragrance compound, a flavor compound or a combination thereof,
wherein said photosensitive poly-unsaturated and/or aromatic compound is stabilized by the method of claim 12.

31. A product which is a cosmetic composition, personal care product or household product which contains at least one photosensitive poly-unsaturated and/or aromatic compound which is either a color compound, antioxidant, a fragrance compound, a flavor compound or a combination thereof,
wherein said photosensitive poly-unsaturated and/or aromatic compound is stabilized by the method of claim 19.

32. A product which is a cosmetic composition, personal care product or household product which contains at least one photosensitive poly-unsaturated and/or aromatic compound which is either a color compound, antioxidant, a fragrance compound, a flavor compound or a combination thereof,
wherein said photosensitive poly-unsaturated and/or aromatic compound is stabilized by the method of claim 21.

33. A product which is a cosmetic composition, personal care product or household product which contains at least one photosensitive poly-unsaturated and/or aromatic compound which is a fragrance compound,
wherein said fragrance compound is stabilized by the method of claim 24.

34. A product which is a cosmetic product which contains at least one photosensitive poly-unsaturated and/or aromatic compound which is a flavor compound,
wherein said flavor compound is stabilized by the method of claim 25.

35. A product of claim 26, which is a household product that is a cleaning composition, detergent, dishwashing liquid or powder, glass or furniture cleaning and/or polishing composition, or floor cleaning and/or polishing composition.

36. A product of claim 30, which is a cosmetic composition, which contains a flavor compound.

37. A product of claim 26, wherein the photosensitive poly-unsaturated and/or aromatic compound is an organic pigment which is a curcuminoid selected from curcumin, Cassumunin A, Cassumunin B, demethoxycurcumin or bis-demethoxycurcumin.

38. A product of claim 25, wherein the photosensitive poly-unsaturated and/or aromatic compound is a carotenoid, tocopherol, guaiazulene, vanillin, menthylanthranillate, ubiquinone, azulene, guaiazulene, or guaiol.

39. A method as in claim 16, wherein the tocopherols are either natural or synthetic or a combination thereof.

40. A method as in claim 39, wherein the tocopherols are a mixture of α, β, γ and δ lipid—soluble tocopherols and α, β, γ and δ lipid-soluble tocotrienols.

41. A method as in claim 39, wherein the tocopherols are a mixture of synthetic DL tocopherols and their acetates.

42. A method for stabilizing photosensitive polymeric thickening agent in a cosmetic composition, personal care product or household product comprising processing at least one compound of formulae ii, ii' and/or i''' and said polymeric thickening agent into said cosmetic composition, personal care product or household product in a ratio within a range of 10:1 to 1:2 based on total weight percent of the one or more compounds of formulae ii, ii' and/or i''' to the total weight percent of the polymeric thickening agent,

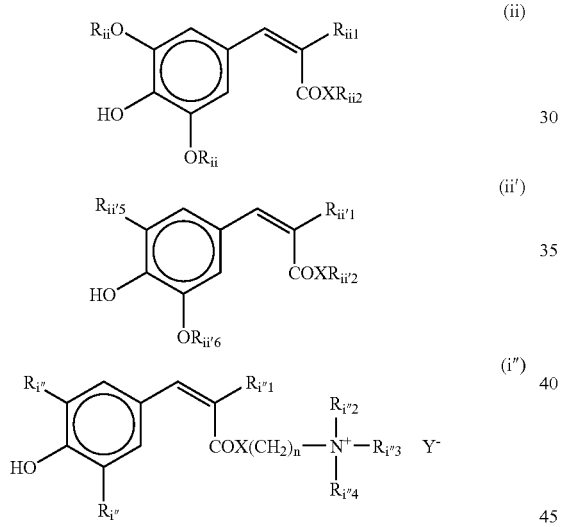

wherein
- each $R_{ii}$ is independently linear or branched $C_1$ to $C_8$ alkyl;
- $R_{ii1}$ is —C(O)CH$_3$, —CO$_2$R$_{ii3}$, —C(O)NH$_2$, —C(O)N(R$_{ii4}$)$_2$, or —CN;
- X is O, NH or N-alkyl;
- $R_{ii2}$ is linear or branched $C_1$ to $C_{20}$ alkyl;
- $R_{ii3}$ is linear or branched $C_1$ to $C_{20}$ alkyl;
- each $R_{ii4}$ is independently hydrogen or linear or branched $C_1$ to $C_8$ alkyl;
- $R_{ii'1}$ is —C(O)CH$_3$, —CO$_2$R$_{ii'3}$, —C(O)NH$_2$, —C(O)N(R$_{ii'4}$)$_2$, or —CN;
- $R_{ii'2}$ is linear or branched $C_1$ to $C_{30}$ alkyl;
- $R_{ii'3}$ is linear or branched $C_1$ to $C_{20}$ alkyl;
- each $R_{ii'4}$ is independently hydrogen or linear or branched $C_1$ to $C_8$ alkyl;
- $R_{ii'5}$ is linear or branched $C_1$–$C_8$ alkyl or hydrogen;
- $R_{ii'6}$ is linear or branched $C_1$–$C_8$ alkyl;
- each $R_{i''}$ is independently linear or branched $C_1$ to $C_8$ alkyl, or linear or branched $C_1$ to $C_8$ alkoxy; or one $R_{i''}$ is H and the other $R_{i''}$ is linear or branched $C_1$ to $C_8$ alkyl, or linear or branched $C_1$ to $C_8$ alkoxy,
- $R_{i''1}$ is COCH$_3$, CO$_2$R$_{i''5}$, CONH$_2$, CONH(R$_{i''6}$)$_2$, CN, COX(CH$_2$)n-N—(R$_{i''2}$)(R$_{i''4}$)(R$_{i''3}$), or the quaternized salt form of the formula COX(CH$_2$)n-N—(R$_{i''2}$)(R$_{i''4}$)(R$_{i''3}$)$^+$Y$^-$,
- n is an integer of 1 to 5,
- Y$^-$ is an anion,
- $R_{i''2}$, $R_{i''3}$ and $R_{i''4}$ are independently linear or branched $C_1$ to $C_{20}$ alkyl; and
- $R_{i''5}$ and $R_{i''6}$ are independently hydrogen or linear or branched $C_1$–$C_{20}$ alkyl.

43. A method according to claim 42, wherein the polymeric thickening agent is a carbomer, acrylate/acrylonitrile copolymer, xanthan gum or a combinations thereof.

44. A method according to claim 42, wherein the ratio of the one or more compound (s) of formulae ii, ii' and/or i''' to the polymeric thickening agent is 5:1 to 1:1.

45. A method according to claim 1, wherein X is N—C$_{1-8}$ Alkyl.

46. A method according to claim 1, wherein X is N-Me.

47. A method according to claim 42, wherein X is N—C$_{1-8}$Alkyl.

48. A method according to claim 42, wherein X is N-Me.

49. A cosmetic composition, personal care product or household product containing a compound of formula ii, ii' and/or i''' within, wherein the at least one compound of formula ii, ii' and/or i''' is used in an amount of about 0.001 to 10.0 wt %, based on the total weight of the cosmetic composition, personal care product or household product

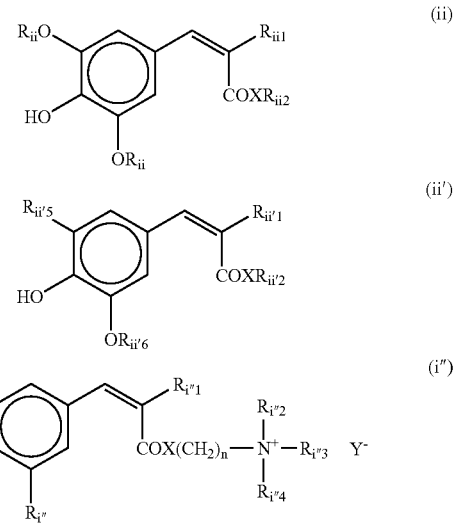

wherein
- each $R_{ii}$ is independently linear or branched $C_1$ to $C_8$ alkyl;
- $R_{ii1}$ is —C(O)CH$_3$, —CO$_2$R$_{ii3}$, —C(O)NH$_2$, —C(O)N(R$_{ii4}$)$_2$, or —CN;
- X is N-alkyl;
- $R_{ii2}$ is linear or branched $C_1$ to $C_{20}$ alkyl;
- $R_{ii3}$ is linear or branched $C_1$ to $C_{20}$ alkyl;
- each $R_{ii4}$ is independently hydrogen or linear or branched $C_1$ to $C_8$ alkyl;
- $R_{ii'1}$ is —C(O)CH$_3$, —CO$_2$R$_{ii'3}$, —C(O)NH$_2$, —C(O)N(R$_{ii'4}$)$_2$, or —CN;

$R_{ii'2}$ is linear or branched $C_1$ to $C_{30}$ alkyl;

$R_{ii'3}$ is linear or branched $C_1$ to $C_{20}$ alkyl;

each $R_{ii'4}$ is independently hydrogen or linear or branched $C_1$ to $C_8$ alkyl;

$R_{ii'5}$ is linear or branched $C_1$–$C_8$ alkyl or hydrogen;

$R_{ii'6}$ is linear or branched $C_1$–$C_8$ alkyl;

each $R_{i''}$ is independently linear or branched $C_1$ to $C_8$ alkyl, or linear or branched $C_1$ to $C_8$ alkoxy; or one $R_{i''}$ is H and the other $R_{i''}$ is linear or branched $C_1$ to $C_8$ alkyl, or linear or branched $C_1$ to $C_8$ alkoxy, $R_{i''1}$ is $COCH_3$, $CO_2R_{i''5}$, $CONH_2$, $CONH(R_{i''6})_2$, CN, $COX(CH_2)n-N-(R_{i''2})(R_{i''4})(R_{i''3})$, or the quaternized salt form of the formula $COX(CH_2)n-N-(R_{i''2})(R_{i''4})(R_{i''3})^+Y^-$, n is an integer of 1 to 5, $Y^-$ is an anion, $R_{i''2}$, $R_{i''3}$ and $R_{i''4}$ are independently linear or branched $C_1$ to $C_{20}$ alkyl; and $R_{i''5}$ and $R_{i''6}$ are independently hydrogen or linear or branched $C_1$–$C_{20}$ alkyl.

50. A composition according to claim 49, wherein X is N—$C_{1-4}$ Alkyl.

51. A composition according to claim 49, wherein X is N-Me.

52. A composition according to claim 49, further containing at least one photosensitive poly-unsaturated and/or aromatic compound which is either a color compound, antioxidant, a fragrance compound, a flavor compound or a combination thereof.

53. A composition consisting essentially of one or more photosensitive poly-unsaturated and/or aromatic compound which are either one or more color compounds, one or more antioxidants, one or more fragrance compounds, one or more flavor compounds or a combination thereof, and one or more compounds of formulae ii, ii' and/or i",

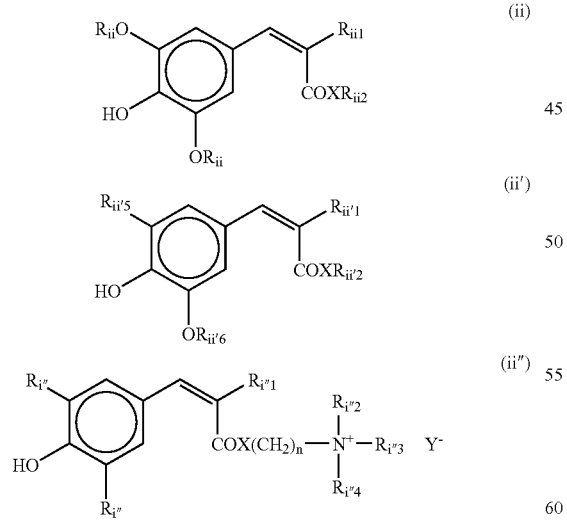

wherein each $R_{ii}$ is independently linear or branched $C_1$ to $C_8$ alkyl;

$R_{ii1}$ is —$C(O)CH_3$, —$CO_2R_{ii3}$, —$C(O)NH_2$, —$C(O)N(R_{ii4})_2$, or —CN;

X is O, NH or N-alkyl;

$R_{ii2}$ is linear or branched $C_1$ to $C_{20}$ alkyl;

$R_{ii3}$ is linear or branched $C_1$ to $C_{20}$ alkyl;

each $R_{ii4}$ is independently hydrogen or linear or branched $C_1$ to $C_8$ alkyl;

$R_{ii'1}$ is —$C(O)CH_3$, —$CO_2R_{ii'3}$, —$C(O)NH_2$, —$C(O)N(R_{ii'4})_2$, or —CN;

$R_{ii'2}$ is linear or branched $C_1$ to $C_{30}$ alkyl;

$R_{ii'3}$ is linear or branched $C_1$ to $C_{20}$ alkyl;

each $R_{ii'4}$ is independently hydrogen or linear or branched $C_1$ to $C_8$ alkyl;

$R_{ii'5}$ is linear or branched $C_1$–$C_8$ alkyl or hydrogen;

$R_{ii'6}$ is linear or branched $C_1$–$C_8$ alkyl;

each $R_{i''}$ is independently linear or branched $C_1$ to $C_8$ alkyl, or linear or branched $C_1$ to $C_8$ alkoxy; or one $R_{i''}$ is H and the other $R_{i''}$ is linear or branched $C_1$ to $C_8$ alkyl, or linear or branched $C_1$ to $C_8$ alkoxy, $R_{i''1}$ is $COCH_3$, $CO_2R_{i''5}$, $CONH_2$, $CONH(R_{i''6})_2$, CN, $COX(CH_2)n-N-(R_{i''2})(R_{i''4})(R_{i''3})$, or the quaternized salt form of the formula $COX(CH_2)n-N-(R_{i''2})(R_{i''4})(R_{i''3})^+Y^-$, n is an integer of 1 to 5, $Y^-$ is an anion, $R_{i''2}$, $R_{i''3}$ and $R_{i''4}$ are independently linear or branched $C_1$ to $C_{20}$ alkyl; and $R_{i''5}$ and $R_{i''6}$ are independently hydrogen or linear or branched $C_1$–$C_{20}$ alkyl.

54. A composition according to claim 53, wherein the ratio of the total weight percent of the one or more compounds of formulae ii, ii' and/or i" to the total weight percent of the at least one photosensitive poly-unsaturated and/or aromatic compound which is either a color compound, antioxidant, a fragrance compound, a flavor compound or a combination thereof, is within a range of 10:1 to 1:2.

55. A composition according to claim 53, containing one or more fragrance compounds.

56. A method of stabilizing an oil and/or wax, said method comprising combining at least one compound of formulae ii, ii' and/or i" with said oil and/or wax, wherein the ratio of the total weight percent of the one or more compounds of formulae ii, ii' and/or i" to the total weight percent of the oil and/or wax, is within a range of 10:1 to 1:2.

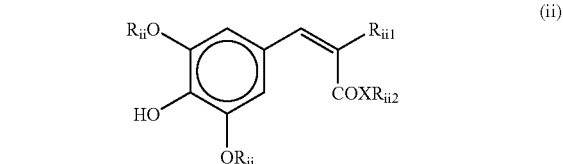

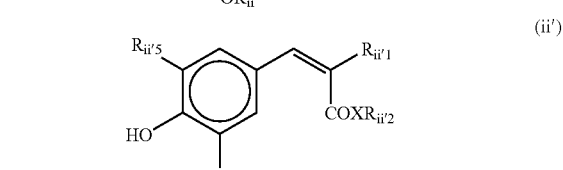

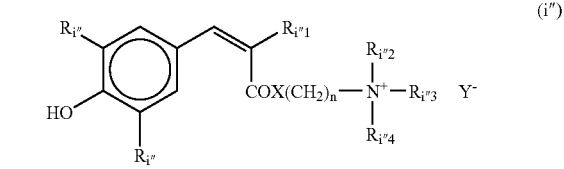

wherein
- each $R_{ii}$ is independently linear or branched $C_1$ to $C_8$ alkyl;
- $R_{ii1}$ is —C(O)CH$_3$, —CO$_2$R$_{ii3}$, —C(O)NH$_2$, —C(O)N(R$_{ii4}$)$_2$, or —CN;
- X is O, NH or N-alkyl;
- $R_{ii2}$ is linear or branched $C_1$ to $C_{20}$ alkyl;
- $R_{ii3}$ is linear or branched $C_1$ to $C_{20}$ alkyl;
- each $R_{ii4}$ is independently hydrogen or linear or branched $C_1$ to $C_8$ alkyl;
- $R_{ii'1}$ is —C(O)CH$_3$, —CO$_2$R$_{ii'3}$, —C(O)NH$_2$, —C(O)N(R$_{ii'4}$)$_2$, or —CN;
- $R_{ii'2}$ is linear or branched $C_1$ to $C_{30}$ alkyl;
- $R_{ii'3}$ is linear or branched $C_1$ to $C_{20}$ alkyl;
- each $R_{ii'4}$ is independently hydrogen or linear or branched $C_1$ to $C_8$ alkyl;
- $R_{ii'5}$ is linear or branched $C_1$–$C_8$ alkyl or hydrogen;
- $R_{ii'6}$ is linear or branched $C_1$–$C_8$ alkyl;
- each $R_{i''}$ is independently linear or branched $C_1$ to $C_8$ alkyl, or linear or branched $C_1$ to $C_8$ alkoxy; or one $R_{i''}$ is H and the other $R_{i''}$ is linear or branched $C_1$ to $C_8$ alkyl, or linear or branched $C_1$ to $C_8$ alkoxy,
- $R_{i''1}$ is COCH$_3$, CO$_2$R$_{i''5}$, CONH$_2$, CONH(R$_{i''6}$)$_2$, CN, COX(CH$_2$)n-N—(R$_{i''2}$)(R$_{i''4}$)(R$_{i''3}$), or the quaternized salt form of the formula COX(CH$_2$)n-N—(R$_{i''2}$)(R$_{i''4}$)(R$_{i''3}$)$^+$Y$^-$,
- n is an integer of 1 to 5,
- Y$^-$ is an anion,
- $R_{i''2}$, $R_{i''3}$ and $R_{i''4}$ are independently linear or branched $C_1$ to $C_{20}$ alkyl; and
- $R_{i''5}$ and $R_{i''6}$ are independently hydrogen or linear or branched $C_1$–$C_{20}$ alkyl.

57. A method of stabilizing a vitamin, said method comprising combining at least one compound of formulae ii, ii' and/or i'' with said oil and/or wax,
wherein the ratio of the total weight percent of the one or more compounds of formulae ii, ii' and/or i'' to the total weight percent of the vitamin, is within a range of 10:1 to 1:2.

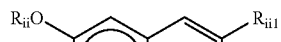

(ii)

(ii')

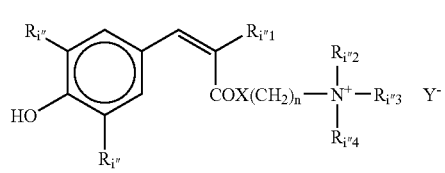

(i'')

wherein
- each $R_{ii}$ is independently linear or branched $C_1$ to $C_8$ alkyl;
- $R_{ii1}$ is —C(O)CH$_3$, —CO$_2$R$_{ii3}$, —C(O)NH$_2$, —C(O)N(R$_{ii4}$)$_2$, or —CN;
- X is O, NH or N-alkyl;
- $R_{ii2}$ is linear or branched $C_1$ to $C_{20}$ alkyl;
- $R_{ii3}$ is linear or branched $C_1$ to $C_{20}$ alkyl;
- each $R_{ii4}$ is independently hydrogen or linear or branched $C_1$ to $C_8$ alkyl;
- $R_{ii'1}$ is —C(O)CH$_3$, —CO$_2$R$_{ii'3}$, —C(O)NH$_2$, —C(O)N(R$_{ii'4}$)$_2$, or —CN;
- $R_{ii'2}$ is linear or branched $C_1$ to $C_{30}$ alkyl;
- $R_{ii'3}$ is linear or branched $C_1$ to $C_{20}$ alkyl;
- each $R_{ii'4}$ is independently hydrogen or linear or branched $C_1$ to $C_8$ alkyl;
- $R_{ii'5}$ is linear or branched $C_1$–$C_8$ alkyl or hydrogen;
- $R_{ii'6}$ is linear or branched $C_1$–$C_8$ alkyl;
- each $R_{i''}$ is independently linear or branched $C_1$ to $C_8$ alkyl, or linear or branched $C_1$ to $C_8$ alkoxy; or one $R_{i''}$ is H and the other $R_{i''}$ is linear or branched $C_1$ to $C_8$ alkyl, or linear or branched $C_1$ to $C_8$ alkoxy,
- $R_{i''1}$ is COCH$_3$, CO$_2$R$_{i''5}$, CONH$_2$, CONH(R$_{i''6}$)$_2$, CN, COX(CH$_2$)n-N—(R$_{i''2}$)(R$_{i''4}$)(R$_{i''3}$), or the quaternized salt form of the formula COX(CH$_2$)n-N—(R$_{i''2}$)(R$_{i''4}$)(R$_{i''3}$)$^+$Y$^-$,
- n is an integer of 1 to 5,
- Y$^-$ is an anion,
- $R_{i''2}$, $R_{i''3}$ and $R_{i''4}$ are independently linear or branched $C_1$ to $C_{20}$ alkyl; and
- $R_{i''5}$ and $R_{i''6}$ are independently hydrogen or linear or branched $C_1$–$C_{20}$ alkyl.

58. A method according to claim 57, wherein the vitamin is Vitamin E, C or K or a derivative thereof.

* * * * *

UNITED STATES PATENT AND TRADEMARK OFFICE
CERTIFICATE OF CORRECTION

PATENT NO. : 7,150,876 B2
APPLICATION NO. : 11/115395
DATED : December 19, 2006
INVENTOR(S) : Ratan K. Chaudhuri Page 1 of 1

It is certified that error appears in the above-identified patent and that said Letters Patent is hereby corrected as shown below:

Column 35, line 19, reads " ... $(CH_2)n-N$ ..." should read -- ... $(CH_2)_n-N$ ... --
Column 35, line 20, reads " ... $(CH_2)n-N$ ..." should read -- ... $(CH_2)_n-N$ ... --
Column 35, line 26, reads "$C_{20}$alkyl;" should read -- $C_{20}$ alkyl; --
Column 42, line 4, reads " ... $(CH_2)n-N$ ..." should read -- ... $(CH_2)_n-N$ ... --
Column 42, line 5, reads " ... $(CH_2)n-N$ ..." should read -- ... $(CH_2)_n-N$ ... --
Column 42, line 15, reads "or a combinations" should read -- or a combination --
Column 43, line 13, reads " ... $(CH_2)n-N$ ..." should read -- ... $(CH_2)_n-N$ ... --
Column 43, line 14, reads " ... $(CH_2)n-N$ ..." should read -- ... $(CH_2)_n-N$ ... --
Column 44, line 19, reads " ... $(CH_2)n-N$ ..." should read -- ... $(CH_2)_n-N$ ... --
Column 44, line 20, reads " ... $(CH_2)n-N$ ..." should read -- ... $(CH_2)_n-N$ ... --
Column 44, line 43, reads "10:1 to 1:2." should read -- 10:1 to 1:2, --
Column 45, line 24, reads " ... $(CH_2)n-N$ ..." should read -- ... $(CH_2)_n-N$ ... --
Column 45, line 25, reads " ... $(CH_2)n-N$ ..." should read -- ... $(CH_2)_n-N$ ... --
Column 45, line 40, reads "to 1:2." should read -- to 1:2, --
Column 46, line 41, reads " ... $(CH_2)n-N$ ..." should read -- ... $(CH_2)_n-N$ ... --
Column 46, line 42, reads " ... $(CH_2)n-N$ ..." should read -- ... $(CH_2)_n-N$ ... --

Signed and Sealed this

Twenty-ninth Day of May, 2007

JON W. DUDAS
*Director of the United States Patent and Trademark Office*